(12) United States Patent
Nightingale et al.

(10) Patent No.: US 7,374,538 B2
(45) Date of Patent: *May 20, 2008

(54) METHODS, SYSTEMS, AND COMPUTER PROGRAM PRODUCTS FOR ULTRASOUND MEASUREMENTS USING RECEIVE MODE PARALLEL PROCESSING

(75) Inventors: Kathryn R. Nightingale, Durham, NC (US); Gregg E. Trahey, Hillsborough, NC (US)

(73) Assignee: Duke University, Durham, NC (US)

( * ) Notice: Subject to any disclaimer, the term of this patent is extended or adjusted under 35 U.S.C. 154(b) by 676 days.

This patent is subject to a terminal disclaimer.

(21) Appl. No.: 10/680,073

(22) Filed: Oct. 6, 2003

(65) Prior Publication Data

US 2004/0167403 A1    Aug. 26, 2004

Related U.S. Application Data

(63) Continuation-in-part of application No. 10/240,909, filed on Feb. 26, 2003, now Pat. No. 6,951,544.

(60) Provisional application No. 60/421,140, filed on Oct. 7, 2002.

(51) Int. Cl.
    *A61B 8/00*    (2006.01)

(52) U.S. Cl. .................................... 600/443

(58) Field of Classification Search ........ 600/437–440, 600/442–447, 462–471; 73/570, 573–574, 73/584, 596, 625–626

See application file for complete search history.

(56) References Cited

U.S. PATENT DOCUMENTS

| | | | |
|---|---|---|---|
| 4,913,157 A | 4/1990 | Pratt et al. | 128/661.03 |
| 5,099,848 A | 3/1992 | Parker et al. | 128/661.07 |
| 5,107,837 A | 4/1992 | Ophir et al. | 128/660.01 |
| 5,411,028 A * | 5/1995 | Bonnefous | 600/454 |
| 5,474,070 A * | 12/1995 | Ophir et al. | 600/437 |
| 5,487,387 A | 1/1996 | Trahey et al. | 125/660.02 |
| 5,524,636 A | 6/1996 | Sarvazyan et al. | 128/774 |
| 5,606,971 A * | 3/1997 | Sarvazyan | 600/438 |
| 5,673,700 A * | 10/1997 | Yamazaki et al. | 600/455 |
| 5,810,731 A | 9/1998 | Sarvazyan et al. | 600/438 |
| 5,848,969 A * | 12/1998 | Panescu et al. | 600/455 |

(Continued)

FOREIGN PATENT DOCUMENTS

WO    98/55025    12/1998

OTHER PUBLICATIONS

Geiman, B.J. et al "A Novel Interpolation Strategy for Estimating Subsample Speckle Motion", Phys. Med. Biol. 45 (2000) pp. 1541-1552.*

(Continued)

*Primary Examiner*—Francis J. Jaworski
(74) *Attorney, Agent, or Firm*—Myers Bigel Sibley & Sajovec, PA

(57) ABSTRACT

A pushing pulse is delivered from an ultrasound transducer array having a plurality of elements to a target region within a medium to displace the target region to a displaced position. A tracking pulse is delivered from the ultrasound transducer array to the target region, and a plurality of tracking signals are received from locations in the target region, each tracking signal being responsive to the tracking pulse.

84 Claims, 16 Drawing Sheets

U.S. PATENT DOCUMENTS

| | | | | |
|---|---|---|---|---|
| 5,921,928 | A | | 7/1999 | Greenleaf et al. ............ 600/437 |
| 5,940,123 | A | * | 8/1999 | Daigle et al. ................ 348/163 |
| 5,991,239 | A | * | 11/1999 | Fatemi-Booshehri et al. ............................. 367/164 |
| 6,039,691 | A | * | 3/2000 | Walker et al. ................ 600/452 |
| 6,113,543 | A | * | 9/2000 | Bonnefous ................... 600/438 |
| 6,165,128 | A | * | 12/2000 | Cespedes et al. ............ 600/463 |
| 6,221,020 | B1 | * | 4/2001 | Lysyansky et al. ........... 600/453 |
| 6,270,459 | B1 | * | 8/2001 | Konofagou et al. ......... 600/449 |
| 6,352,507 | B1 | * | 3/2002 | Torp et al. ................... 600/438 |
| 6,371,912 | B1 | * | 4/2002 | Nightingale et al. ......... 600/437 |
| 6,448,626 | B1 | * | 9/2002 | Yoon ............................ 257/529 |
| 6,488,626 | B1 | * | 12/2002 | Lizzi et al. ................... 600/437 |
| 6,494,834 | B2 | * | 12/2002 | Konofagou et al. ......... 600/438 |
| 6,520,913 | B1 | * | 2/2003 | Ermert et al. ................ 600/438 |
| 6,561,981 | B2 | * | 5/2003 | Bonnefous ................... 600/443 |
| 6,716,168 | B2 | * | 4/2004 | Nock et al. ................... 600/439 |
| 6,749,571 | B2 | * | 6/2004 | Varghese et al. ............. 600/450 |
| 6,764,448 | B2 | * | 7/2004 | Nightingale et al. ......... 600/437 |
| 6,951,544 | B2 | * | 10/2005 | Trahey et al. ................ 600/449 |

OTHER PUBLICATIONS de Korte, C.L. et al, "A Novel Interpolation Strategy for Estimating Subsample Speckle Motion ", Phys. Med. Biol. 45 (2000), pp. 1465-1475.*

Supplementary Partial European Search Report for EP Application 01 93 0447 dated Feb. 2, 2005.

International Search Report; PCT/US01/11051; filed Apr. 2001.

A. Saravazyan et al., Biophysical Bases of Elasticity Imaging, *Acoustic Imaging* 21, 223-240 (1995).

K. Nightingale, *Ultrasonic Generation and Detection of Acoustic Streaming to Differentiate Between Fluid-Filled and Solid Lesions in the Breast* (Ph.D. Thesis, Duke University, Sep. 1997).

K. Nightingale, R. Nightingale, T. Hall, and G. Trahey, The use of radiation force induced tissue displacements to image stiffness: a feasibility study, 23$^{rd}$ International Symposium on Ultrasonic Imaging and Tissue Characterization, May 27-29, 1998.

Krouskop et. al., Elastic Moduli of Breast and Prostate Tissues Under Compression *Ultrasonic Imaging* 260-274 (1998).

M. Fatemi and J. Greenleaf, Ultrasound-stimulated vibro-acoustic spectrography, *Science*, 280:82-85, (1998).

K.R. Nightingale, R.W. Nightingale, M.L. Palmeri, and G.E. Trahey, Finite element analysis of radiation force induced tissue motion with experimental validation, In *Proceedings of the 1999 IEEE Ultrasound Symposium*, page in press, 1999.

K Nightingale et al., Utilization of Acoustic Streaming to Classify Breast Lesions In Vivo. *Proceedings of the 1997 IEEE Ultrasonic Symposium*, 1419-1422 (Toronto, CA, Oct. 1997).

A. Sarvazyan, O. Rudenko, S. Swanson, J. Fowlkes, and S. Emelianov, Shear wave elasticity imaging: A new ultrasonic technology of medical diagnostics, *Ultrasound Med. Biol.* 24:9 1419-1435 (1998).

T. Sugimoto, S. Ueha, and K. Itoh, Tissue hardness measurement using the radiation force of focused ultrasound, In *Proceedings of the 1990 Ultrasonics Symposium*, pp. 1377-1380, 1990.

W. Walker, Internal deformation of a uniform elastic solid by acoustic radiation force, *J. Acoust. Soc. Am.*, 105:4 2508-2518 (1999).

* cited by examiner

US 7,374,538 B2

METHODS, SYSTEMS, AND COMPUTER PROGRAM PRODUCTS FOR ULTRASOUND MEASUREMENTS USING RECEIVE MODE PARALLEL PROCESSING

RELATED APPLICATIONS

This application is a continuation-in-part application of U.S. application Ser. No. 10/240,909, submitted on Oct. 4, 2002, now U.S. Pat. No. 6,951,544, and having a §371(c) filing date of Feb. 26, 2003, which claims the benefit of PCT Application PCTUS0111051 filed Apr. 5, 2001, U.S. patent application Ser. No. 09663271 (now issued U.S. Pat. No. 6,371,912), filed Sep. 18, 2000, and U.S. Provisional Application Ser. No. 60/194,746, filed Apr. 5, 2000. This application also claims the benefit of U.S. Provisional Application Ser. No. 60/421,140, filed Oct. 7, 2002. The disclosures of the above patents and patent applications are hereby incorporated by reference herein in their entirety.

GOVERNMENT SUPPORT

This invention was made with Government support under grant number DAMD17-98-1-8068 from the Department of Defense and grant number R01-CA-92183 (renamed R01-EB002132) from National Institute of Health. The Government has certain rights to this invention.

FIELD OF THE INVENTION

The present invention concerns methods and apparatus for the identification and characterization of regions of different mechanical properties in a target media, such as a biological tissue.

BACKGROUND OF THE INVENTION

The early detection of diseases, such as cancer and heart disease, may significantly improve patient survival. For example, present methods of breast cancer detection include screening mammography and palpation, either by patient self-examination or clinical breast exam. Palpation relies on the manual detection of differences in tissue stiffness between breast lesions and normal breast tissue. The success of palpation is due to the fact that the elastic modulus (or Young's modulus) of malignant tumors is often an order of magnitude greater than that of normal breast tissue. That is, cancerous lesions feel "hard" or "stiff" as compared to normal breast tissue. See T. Krouskop et al., *Ultrasonic Imaging* 20, 260-274 (1998); A. Saravazyan et al., *Acoustic Imaging* 21, 223-240 (1995).

As another example, atherosclerosis is a medical condition that involves the stiffening of the arteries, which can occur prior to and in addition to the formation of focal lesions. A human artery has three layers. The innermost layer is relatively thin compared to the other two layers and is commonly referred to as the endothelium layer or intimal layer. The middle layer is a smooth muscle layer (media layer), and the outer layer is a connective tissue layer (adventita). Atherosclerosis can be caused by plaque build up between layers in the arteries, which can lead to conditions that include blockages in blood flow, poor circulation, myocardial infarction, aneurisms, and stroke. The development of atherosclerosis can be influenced by factors such as diet, exercise, smoking habits, and other medical conditions such as diabetes. Treatments for atherosclerosis include drug therapy, changes in diet, increased exercise programs, and smoking cessation.

Focal lesions, which protrude into the blood vessel, may be detected by a variety of methods, including cardiac catheterization, intravascular ultrasound, conventional B-mode and Color Doppler ultrasound, and electron beam computed tomography. However, atherosclerosis may occur prior to the formation of focal lesions and does not necessarily involve plaque protrusions that could be detectable using conventional testing methods. Atherosclerosis may also be characterized by increased blood pressure. However, blood pressure levels do not directly correlate to degrees of atherosclerosis, and elevated blood pressure levels may not exist in a subject without atherosclerosis.

U.S. Pat. No. 5,921,928 to Greenleaf uses sound waves to vibrate tissue and monitors the response of the vibrating tissue. A disadvantage of such an approach is that different transmit and detection systems may be required, and multiple pushing cycles at a single location may be required. Moreover, ultrasonic stimulated acoustic emissions may not result in a form feasible for actual clinical diagnosis.

SUMMARY OF THE INVENTION

According to some embodiments of the invention, methods, systems, and computer program products are provided. In some embodiments, a pushing pulse is delivered from an ultrasound transducer array having a plurality of elements to a target region within a medium to displace the target region to a displaced position. A tracking pulse is delivered from the ultrasound transducer array to the target region, and a plurality of tracking signals are received from locations in the target region, each tracking signal being responsive to the tracking pulse. The received tracking signals can be received in parallel receive mode, including parallel receive mode in the time domain and/or frequency domain, and can include parallel beam formed signals.

In further embodiments, a first tracking pulse is delivered from an ultrasound transducer array to a target region within a medium. A first set of tracking signals from locations in the target region and responsive to the tracking pulse in the target region is received at the ultrasound transducer array to detect an initial position for the target region. A pushing pulse is delivered from the ultrasound transducer array to the target region to displace the target region to a displaced position. A second tracking pulse is delivered from the ultrasound transducer array to the target region. A second set of tracking signals from locations in the target region is received responsive to the second tracking pulse at the ultrasound transducer array to detect the displaced position of the target region. Delivering a first tracking pulse, receiving a first tracking signal, delivering a pushing pulse, delivering a second tracking pulse, and receiving a second tracking signal can be repeated sequentially to provide a series of cycles. The pushing pulses can be delivered to different target regions during the series of cycles to provide a plurality of displaced positions.

In some embodiments a blood vessel and/or cardiac tissue in a subject can be evaluated by detecting a mechanical property of a vessel wall and/or cardiac tissue to provide at least first and second values associated with the mechanical property at at least two timing points during a cardiac cycle of the subject. The first and second values can be compared, for example, to evaluate the cardiac health of the subject.

In further embodiments, a blood vessel and/or cardiac tissue in a subject can be evaluated by detecting a first value associated with a mechanical property of a vessel wall and/or cardiac tissue at a first spatial point within a first layer of the vessel wall and/or cardiac tissue. A second value associated with the mechanical property at a second spatial point of the vessel wall and/or cardiac tissue within a second layer of the vessel wall and/or cardiac tissue can be detected. The first and second values can be compared.

While the invention has been described above primarily with respect to the various method aspects of the invention, both systems and/or computer program products are also provided.

DETAILED DESCRIPTION OF THE PREFERRED EMBODIMENTS

The present invention now will be described more fully hereinafter with reference to the accompanying drawings, in which illustrative embodiments of the invention are shown. This invention, however, should not be construed as limited to the embodiments set forth herein; rather, these embodiments are provided so that this disclosure will be thorough and complete, and will fully convey the scope of the invention to those skilled in the art.

Embodiments of the present invention can use interrogation techniques to characterize a target region, such as to identify regions of greater or lesser stiffness in biological tissue. Ultrasound interrogation techniques used to interrogate blood vessels using receive mode parallel signal processing are first described. Then, various interrogation techniques applied to a target region, such as biological tissue, are described. Then, receive mode parallel processing techniques are described in greater detail. Various techniques used to study blood vessels are discussed.

Receive Mode Parallel Processing Ultrasound Techniques to Interrogate Blood Vessels According to embodiments of the present invention described with reference to FIG. 1, ultrasound techniques using receive mode parallel processing can be used to interrogate blood vessels. It will be understood that various elements and techniques can be used independently of other elements and techniques illustrated in FIG. 1. For example, ultrasound interrogation techniques can be used with or without receive mode parallel processing. Ultrasound interrogation techniques can also be used to interrogate other types of tissue, such as cardiac tissue, muscle tissue, kidneys, breast tissue, or other biological tissue.

Figure 1:
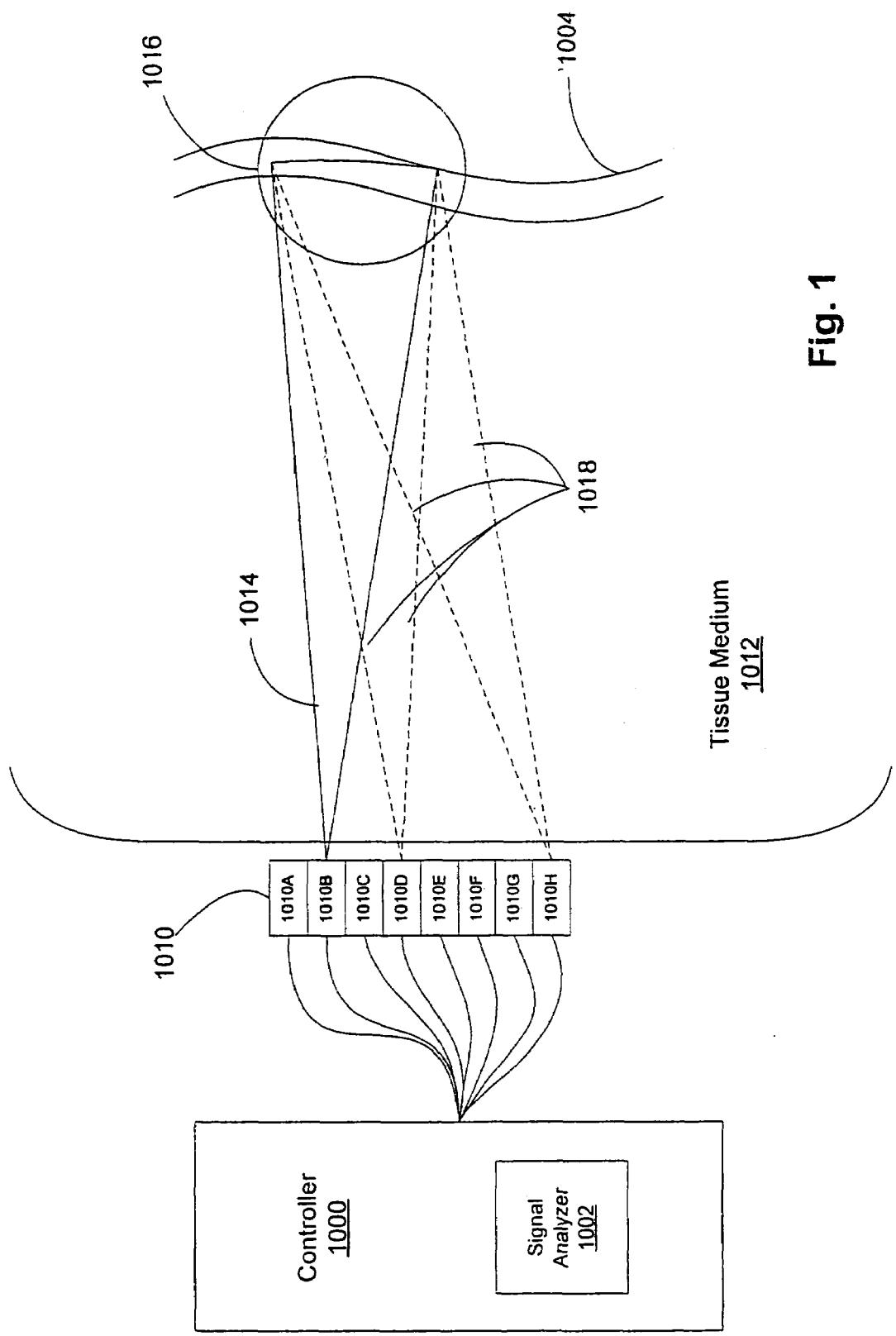
FIG. 1 is a schematic diagram of systems for evaluating blood vessels using an ultrasound transducer array and parallel receive mode processing according to embodiments of the present invention.

Referring to FIG. 1, an ultrasound array 1010 for interrogating a target region 1016 of a tissue medium 1012 that includes a blood vessel 1004 is provided. The ultrasound array 1010 includes transducer elements 1010A-1010H connected to a controller 1000. The controller 1000 can control pulses produced by the transducer elements 1010A-1010H and can include a signal analyzer 1002 for analyzing ultrasound signals received by the transducer elements 1010A-1010H. The signal analyzer 1002 can use receive mode parallel processing techniques to analyze signals from array elements 1010A-1010H. Any number of array elements 1010A-1010H can be provided, including a single transducer and one or two dimensional transducer array configurations. It should be understood that embodiments of the present invention are not limited to the configuration shown in FIG. 1. Certain elements shown in FIG. 1 can be omitted or the functionality of certain elements can be combined with other elements. For example, the signal analyzer 1002 can be provided as part of the controller 1000 or the signal analyzer 1002 can be provided as a separate component from the controller 1000.

As shown in FIG. 1, each element 1010A-1010H in the array 1010 can produce an ultrasound pulse 1014 that propagates through the tissue medium 1012 to the blood vessel 1004 in the target region 1016. The ultrasound pulse 1014 creates a reflected ultrasound wave. In some instances, the ultrasound pulse 1014 can be delivered at an intensity sufficient to cause movement of the target region 1016. When the ultrasound pulse 1014 reaches a reflective boundary between tissues (e.g. between fluid and soft tissue, soft tissue and bone, etc.), some portion of the sound waves are reflected back to the ultrasound array 1010, whereas a remaining portion of the pulse propagates potentially reaching another reflective boundary. Ultrasound waves that may be reflected from within the tissue medium 1012 can be received as a signal by the ultrasound array 1010. As shown in FIG. 1, the reflected waves can be received by one or more array elements 1010A-1010H along exemplary directions 1018. Accordingly, the reflected signals can be received at the array elements 1010A-1010H in a plurality of positions, such as shown, for example, with respect to array elements 1010D and 1010H. The signals can be received from locations within the target region 1016. The signal analyzer 1002 analyzes the signals received by the ultrasound array 1010, for example, to calculate the distances from the array 1010 to the point at which the ultrasound waves were reflected and the intensities of the various reflected waves.

As illustrated for clarity and ease of representation, the pulse 1014 is produced by element 1010B and the reflected ultrasound wave directions 1018 illustrate signals received by array elements 1010D and 1010H. However, it should be understood that each element 1010A-1010H can produce a propagation pulse, such as pulse 1014, and/or receive reflected wave signals, such as waves propagating along directions 1018. Accordingly, the pulse 1014 produced by element 1010B may result in reflected wave signals that can be received by any combination of element(s) 1010A-1010H. Moreover, in some embodiments, a single transducer element can produce a pulse and, in turn, receive the reflection wave signal.

As shown in FIG. 1, the pulse 1014 can be a de-focused beam with respect to the target region 1016. The reflected waves can be received from various locations in the target region 1016 and processed in parallel, for example, using a time-delayed signal to take into account varying distances between the origin of the reflected wave and each ultrasound transducer element 1010A-1010H. The time delay can be configured so that the reflected waves recorded by each transducer are in phase before they are summed and/or analyzed. Thus, the resulting signal can be a sum of focal delayed signals received at each of the transducer elements 1010A-1010H. Multiple sums of differently focused delayed signals can be used for a single pulse. Accordingly, increased information may be obtained for a single pulse, which can result in increased frame-rates and/or reduced tissue heating.

In some embodiments, a pulse or a series of pulses can be produced by various elements 1010A-1010H in the ultrasound array 1010 to remotely characterize tissue stiffness, such as by using a pulse with sufficient ultrasonic radiation force so as to displace the target region 1016. One particular approach is referred to as remote palpation. In remote palpation, acoustic radiation force is used to apply localized forces within tissue, and the resulting tissue displacements are mapped using either ultrasonic correlation based methods, or other pattern matching methods. A volume of tissue that is stiffer than the surrounding medium (i.e., a lesion) may distribute the force throughout the tissue beneath it, resulting in larger regions of displacement, and smaller maximum displacements. Remote palpation is described in K. Nightingale, *Ultrasonic Generation and Detection of Acoustic Streaming to Differentiate Between Fluid-Filled and Solid Lesions in the Breast* (Ph.D. Thesis, Duke University, September 1997), and in K Nightingale et al., *Proceedings of the* 1997 *IEEE Ultrasonics Symposium*, 1419-1422 (Toronto, Calif., October 1997). Another approach is referred to as acoustic radiation force impulse ("ARFI"), which uses ultrasound pulses to push on tissue, and subsequently measures the mechanical response of the tissue. Various ARFI techniques are disclosed in U.S. Pat. No. 6,371,912 to Nightingale et al., the disclosure of which is hereby incorporated by reference in its entirety.

In some embodiments of the present invention using ARFI techniques, a "pushing" pulse can be delivered from the ultrasound array 1010 to displace the target region 1016 such that the displacement of the target region can be detected. A "tracking" pulse can be delivered from the ultrasound transducer array 1010 to the target region 1016. The tracking pulse and/or the pushing pulse may be represented by pulse 1014 as shown in FIG. 1. A tracking signal, such as the reflected ultrasound wave, can be received by the ultrasound array 1010 from a plurality of directions 1018. If a tracking pulse is broadly focused, a plurality of tracking signals can be received at the transducer array 1010. The tracking signal can be used to detect the displaced position of the target region 1016. Regions of altered stiffness can be detected, for example, based on characteristics of the displacement at various locations detected in the target region 1016. In some embodiments according to the invention, the tracking signals received from locations in the target region 1016 and responsive to the tracking pulse may be processed using receive mode parallel processing techniques. For example, the tracking signals can be parallel beam formed signals. Time domain and frequency domain receive mode parallel processing techniques can be used. For example, multiple sums of differently focused delayed signals received at each of the plurality of elements in the ultrasound transducer array can be used. Accordingly, receive mode parallel processing techniques can result in increased frame-rates and/or reduced tissue heating.

In some embodiments, an initial tracking pulse can be delivered from the ultrasound transducer array 1010 to the target region 1016 prior to the pushing pulse. An initial tracking signal responsive to the initial tracking pulse can be received to detect an initial position for the target region. A difference between the initial position and a displaced position can be used to detect regions of varying degrees of stiffness. For example, a region of decreased displacement relative to other regions can indicate that the region of decreased displacement has a greater stiffness relative to other regions. A region of lesser stiffness can be detected by an indication that the region has greater displacement relative to other regions.

The tracking pulse(s) and the pushing pulse can be delivered at different intensity levels so that the intensity level of the pushing pulse is greater than the intensity level of the tracking pulse. For example, the intensity level of the pushing pulse can be between about 1.0 or 10.0 W/cm$^2$ and about 1000.0 or 10,000.0 W/cm$^2$, and the intensity level of the tracking pulse can be less than about 1.0 W/cm$^2$ or about 0.72 W/cm$^2$. The pushing pulse can be delivered for between about 0.025 or lower to about 0.5 milliseconds or more (for example, up to about 10 milliseconds) at various intensity levels. The intensity level can be selected based on the length of the delivered pulse. In some embodiments, transmitting a tracking pulse and receiving a tracking signal can be repeated for a single pushing pulse. For example, an initial position can be detected by an initial tracking pulse prior to the pushing pulse, and a plurality of displaced positions can be detected by a plurality of subsequent tracking pulses after the delivery of the pushing pulse.

As shown in FIG. 1, the target region 1016 includes a blood vessel 1004. Other media can be used, including biological tissue such as breast tissue, muscle tissue or cardiac tissue. Embodiments according to the present invention can be used to detect a region of greater stiffness in biological tissue including tumors, hardened blood vessels, or muscle tissue with greater muscle tone.

For example, blood vessels (such as blood vessel 1004) and/or cardiac tissue in a subject can be evaluated by detecting a value associated with a mechanical property of a vessel wall and/or cardiac tissue to provide at least two values associated with the mechanical property at two or more timing points during a cardiac cycle of the subject. The values associated with the mechanical property can be compared, for example, to evaluate cardiac and/or vascular health. As another example, values associated with a mechanical property of a vessel wall and/or cardiac tissue can be detected at spatial points in different layers in a vessel wall and/or cardiac tissue. The values of the mechanical property at the different spatial points can be compared to evaluate cardiac and/or vascular health. The values associated with the mechanical properties can be detected using ultrasound techniques as described herein.

Ultrasound Interrogation Techniques

Figure 2:
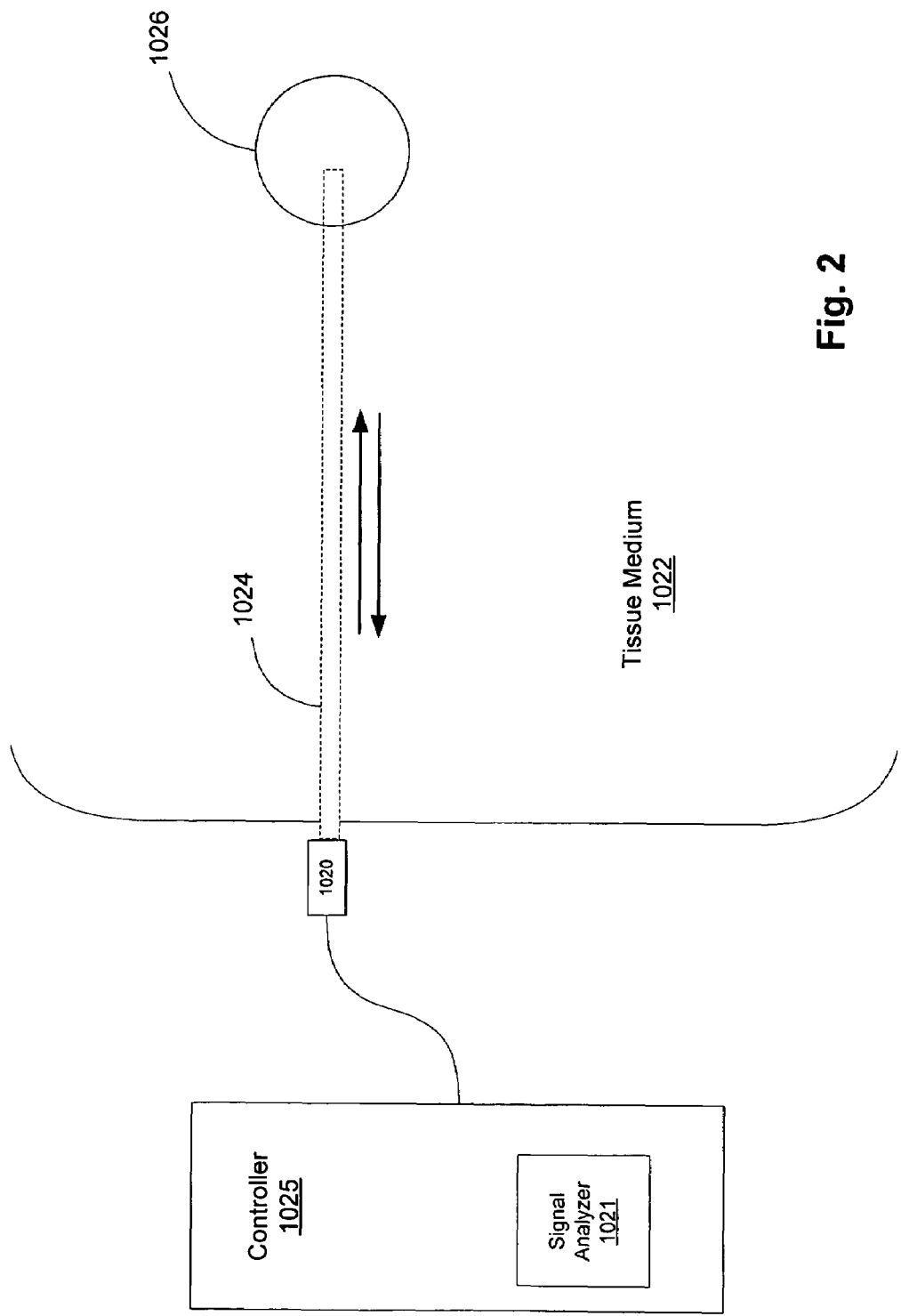
FIG. 2 is a schematic diagram of systems for evaluating a target region using ultrasound interrogation techniques according to further embodiments of the present invention.

Further embodiments according to the present invention are shown in FIG. 2. A controller 1025 including a signal analyzer 1021 is connected to an ultrasound transducer 1020. The controller 1025 can control the transducer 1020 to deliver a pulse along a propagation path 1024 to a target region 1026 in a tissue medium 1022. A reflected wave can travel along the propagation path 1024 to be received by the transducer. The pulses can include "tracking" or "pushing" pulses, and the reflected wave can be a tracking signal.

Figure 3:
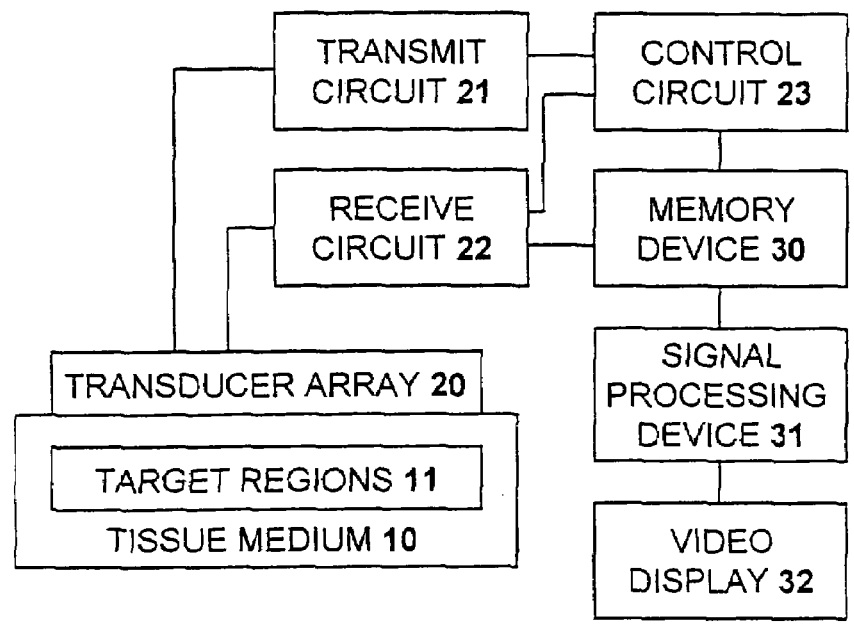
FIG. 3 is a block diagram illustrating further systems using ultrasound interrogation techniques according to further embodiments of the present invention.

As shown in FIG. 3, an exemplary ultrasound transducer array 20 is provided. The ultrasound transducer array 20 may be a one-dimensional array or a two-dimensional array. The ultrasound transducer array 20 may be contacted to a target medium, such as a tissue medium 10. The array can be directed to a two-dimensional plane comprising one or more, and in some embodiments, a plurality of, target regions 11 within the tissue medium. A transmit circuit 21 may be operatively associated with the transducer array to deliver high energy "pushing" pulses to a forcing region among the target regions (i.e., pulses that can induce a physical displacement of the tissue within the target regions), as well as for delivering relatively lower energy "tracking" pulses. A receive circuit 22 can be connected to the transducer array 20 to receive information from the target regions 11 for subsequent signal processing. The transmit circuit 21 and detector circuit 22 may both be operatively associated with an appropriate control circuit 23 that triggers the pushing pulses and tracking pulses, organizing information received from the target regions for subsequent signal processing, and which also cycles the pushing pulses and corresponding tracking pulses through different forcing regions.

Information received by receive circuit 22 can be stored in a memory device 30 such as a random access memory or other suitable memory device, which serves as a medium for storing both initial and displaced positions of target regions. A signal processing device or signal processor 31 is operatively associated with the memory device 30, and can generate initial images for particular forced regions and a single combined image for a plurality of forced regions.

According to embodiments of the present invention, one or more of the following functionalities may be provided:

(a) delivering a set of tracking pulses from a plurality of transducer elements in an ultrasound transducer array to one or a plurality of target regions in a two-dimensional plane within said medium to detect an initial positions for said one or plurality of target regions;

(b) storing said initial positions for said one or plurality of target regions; then (c) delivering a first set of pushing pulses from said plurality of transducer elements to a forcing region among said target regions to displace said target regions to subsequent (e.g., displaced) positions;

(d) delivering a second set of tracking pulses from said plurality of transducer elements in said ultrasound transducer array to said one or plurality of target regions to detect subsequent positions for said one or plurality of target regions, (e) storing said displaced positions for said one or plurality of target regions;

(f) repeating steps (a) through (e) in a series of cycles, with said pushing and tracking pulses being delivered from a different plurality of transducer elements or the same plurality of transducer elements in said array to a different forcing region, and preferably to a plurality of different target regions, during each of said cycles;

(g) generating a two-dimensional displacement map from each of said initial positions and displaced positions for each of said forcing regions to produce a plurality of two-dimensional displacement maps; and then (h) combining said plurality of two-dimensional displacement maps into a single combined image, with a region of increased stiffness being indicated by a region of decreased displacement within said combined image, or a region of decreased stiffness being indicated by a region of increased displacement within said combined image.

Step (d) above may optionally be carried out while concurrently delivering an interspersed set of pushing pulses to said forcing region to reduce the return of said target regions from said displaced positions to said initial positions.

Steps (a) through (e) above may be completed in a total of 50, 25 or 10 milliseconds or less for each cycle (i.e., each forced region). In some embodiments, a cycle of steps (a) through (d) can be completed in 15 milliseconds or less.

In some embodiments, the pushing pulses are delivered before the first set of tracking pulses, the initial positions are displaced positions, and the second positions are relaxed positions. In another embodiment, the pushing pulses are delivered between the first and second set of pulses, the initial positions indicate the relaxed positions, and the second positions indicate the displaced positions.

Figure 4:
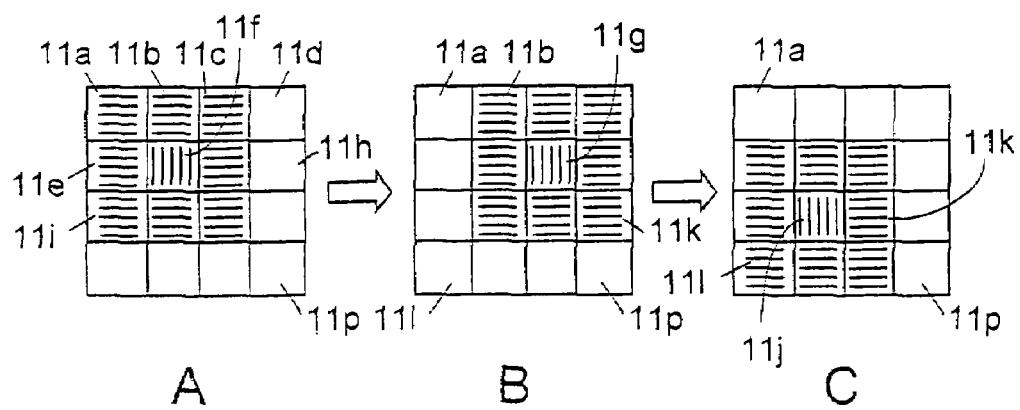
FIG. 4 illustrates the sequential scanning of the two dimensional plane of target regions of FIG. 3, with different forced regions in each cycle, to produce a two dimensional displacement map for each forced region.
Figure 6:
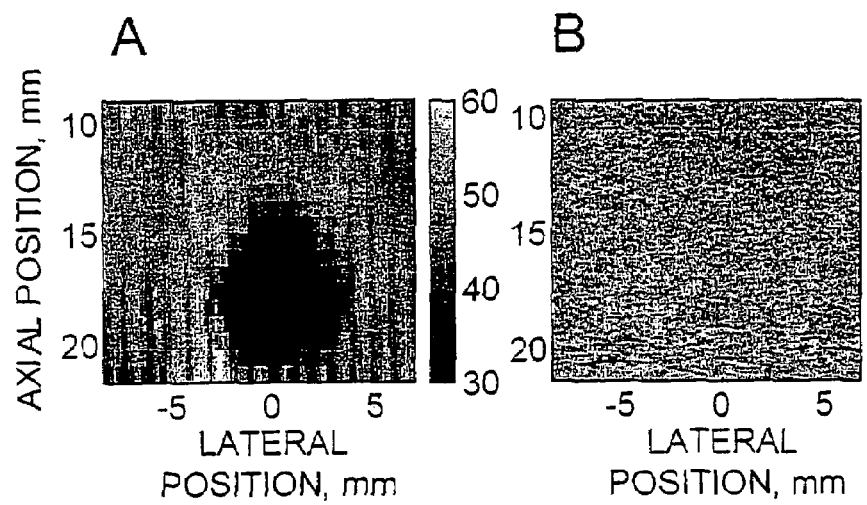
FIG. 6A, is an example remote palpation image of a breast lesion phantom.
FIG. 6B is the corresponding B-mode image of the breast lesion phantom shown in FIG. 6A.
Figure 7:
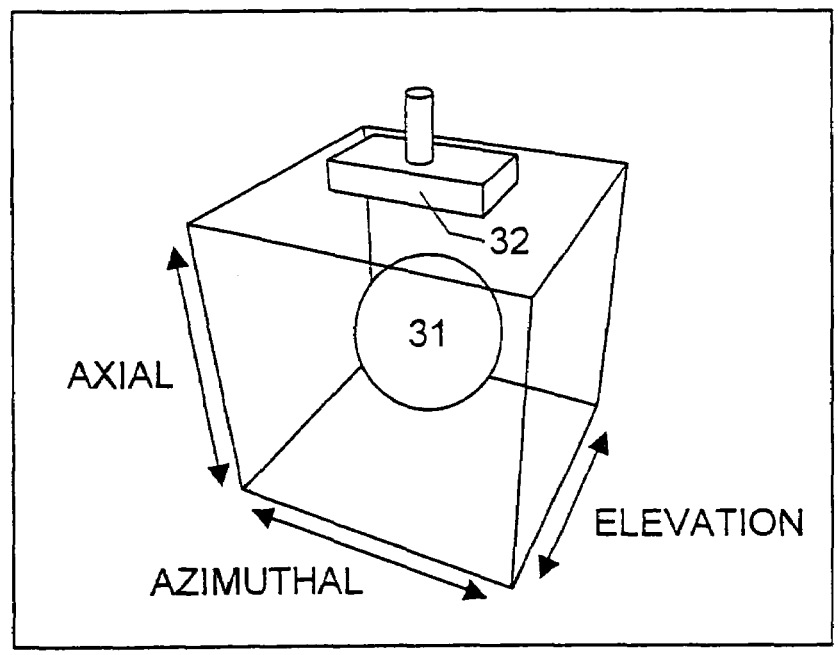
FIG. 7 illustrates embodiments of an orientation of a transducer and the associated different dimensions: axial, azimuthal, and elevation.

FIG. 4 illustrates the cyclic repeating of steps (*a*) through (*e*) above for different forced regions (vertical hatched regions 11*f*, 11*g*, and 11*j*) within the target regions (11*a* through 11*p*) in the axial/azimuthal plane (see FIG. 7). The Boxes represent the same view as that shown in FIG. 6. Arrows represent transition from one cycle to another (cycles A, B, and C). Note that not all target regions need be detected during each cycle, and hence the corresponding transducer elements may be active or inactive in various patterns during each cycle.

Figure 5:
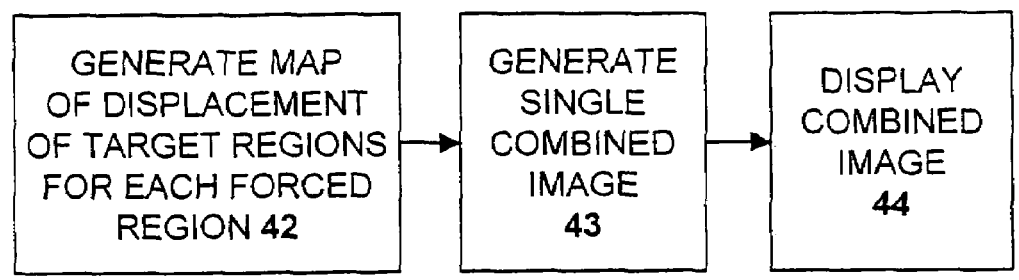
FIG. 5 illustrates the signal processing operations implemented by the signal processing device (31) of FIG. 3, in which the two dimensional displacement maps for each forced region, as generated in FIG. 4, are combined into a single image.

As shown in Block 42 of FIG. 5, a two-dimensional displacement map can then be generated for each cycle A, B, and C of FIG. 4. These two-dimensional displacement maps are then used to generate a single combined image (Block 43) in the signal processing device 31 of FIG. 3. This combined image can then be displayed (Block 44) on the video display device 32 of FIG. 3. Of course, the single combined image may also be stored in a suitable memory device for future reference, printed on a printer, etc. The method may further include generating a B-mode image of the two dimensional plane in accordance with conventional techniques, and then displaying the single combined image superimposed on that B-mode image.

Some embodiments of the invention can be implemented on a Siemens Elegra ultrasound scanner, modified to provide control of beam sequences and access to raw radio frequency data. A Siemens 75L40 transducer may be used as the transducer array.

Some embodiments of the invention may be carried out as follows:

First, a group of low intensity "tracking lines" that interrogate the tissue surrounding the position of interest are fired and stored for tissue initial position reference.

Second, a series of one or more focused, high intensity "pushing lines" is fired along a single line of flight focused at the position of interest.

Third, the original group of tracking lines is fired again, in order to determine the relative motion caused by the radiation force associated with the pushing lines. These tracking lines may optionally be interspersed with pushing lines in order to reduce or avoid relaxation of the tissue.

Fourth, each tracking line is divided into sequential axial search regions, and the displacements of the tissue within each search region are determined. A number of different motion tracking algorithms can be used to determine the relative motion, or displacement, between the initial reference tracking lines and the second set of tracking lines fired after radiation force application. Examples include, but are not limited to, cross correlation and Sum Absolute Difference (SAD). The a priori knowledge of the direction of motion reduces the algorithm implementation time.

Steps 1-4 above are preferably accomplished in 50, 25 or 10 milliseconds or less. The results of step 4 are used to generate a two-dimensional displacement map of the region of tissue surrounding the position of interest (or force location).

Fifth, steps 1 through 4 can be repeated, cyclically, for a plurality of force locations within a larger two-dimensional imaging plane. The number of forcing locations and the spatial distribution of the forcing locations may be determined by (among other things) the specific transducer, transmit parameters, and the size of the region of interest to be interrogated. The same or different sets of elements within the transducer array may be used for the tracking pulses with each force location.

Sixth, each of the two dimensional displacement maps (each of which may be generated before, during or after subsequent cyclical repeatings of steps 1-4) can be combined into a single image (which may or may not be displayed on a video monitor, printer or other such display means). Signal processing such as averaging of collocated regions, and/or some type of normalization to account for the displacement generated in a homogeneous region of tissue, may be employed.

According to some embodiments of the invention, the displacement of the tissue may be monitored over time, both while the force is being applied (by interspersing the pushing lines and the tracking lines), and after cessation of the high intensity pushing lines or pulses. This may be accomplished by firing the group of tracking lines repeatedly at the desired time intervals, and evaluating the changes in the displacement maps over time.

FIG. 6A is an example remote palpation image of a breast lesion phantom. This image was generated using multiple forcing locations, separated by 1 millimeter (mm) in both the axial and azimuthal dimensions. The image spans a 9 ×11 mm region, for a total of 99 different pushing locations. FIG. 6B provides the corresponding B-mode image.

It has been observed that some tissues can exhibit strain-stiffening behavior (i.e. glandular tissue, carcinoma) whereas other tissues do not (i.e. fatty breast tissue). Therefore, in methods intended to characterize the stiffness of tissue, it is often advantageous to pre-compress the tissue. This has the effect of increasing the contrast between the different tissue types (Krouskop et. al., Elastic Moduli of Breast and Prostate Tissues Under Compression, *Ultrasonic Imaging* 20, 260-274 (1998)). This will also be the case for the methods described herein.

Figure 8:
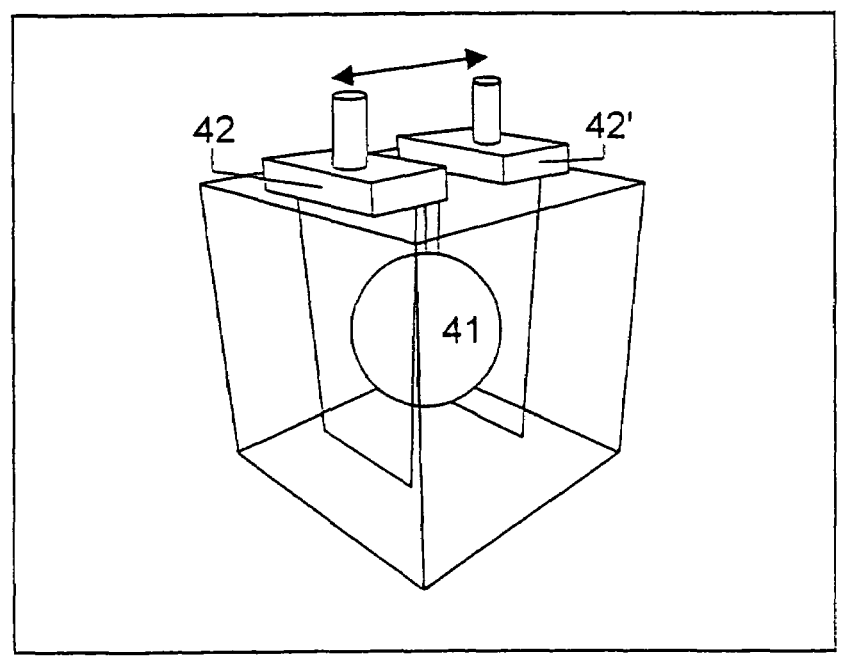
FIG. 8 illustrates embodiments of generating a three-dimensional volume using a translation stage connected to the transducer, which can allow the interrogation of multiple axial/azimuthal planes by translating the transducer in the elevation dimension.
Figure 9:
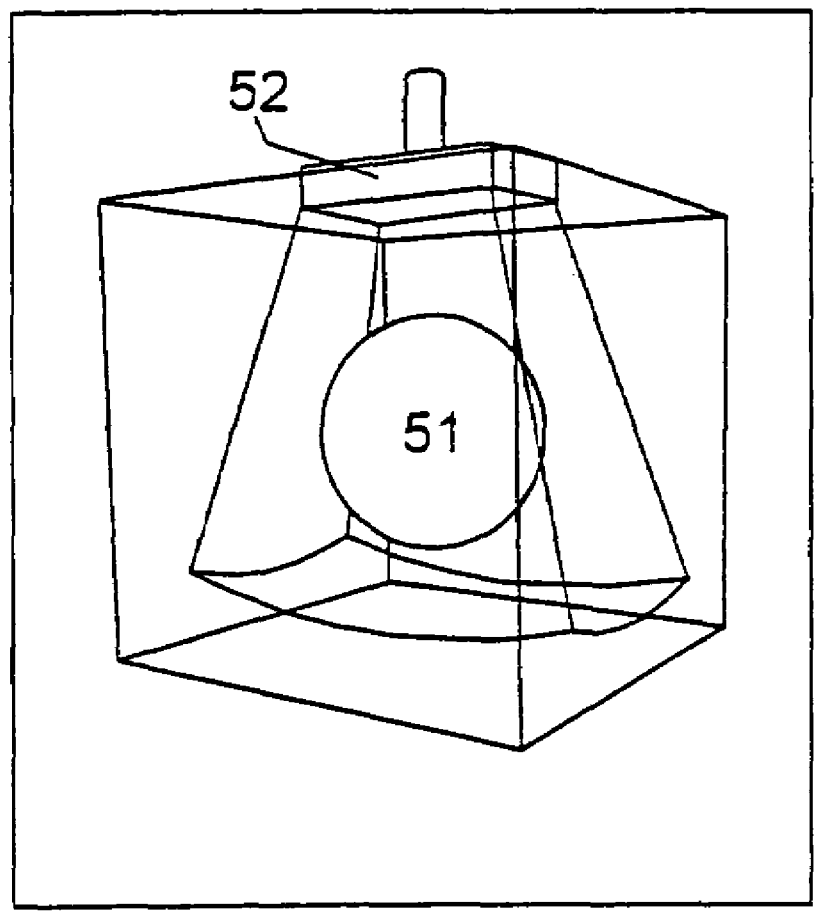
FIG. 9 illustrates embodiments of a two-dimensional transducer (which has several rows of elements) to interrogate a three-dimensional volume.

For clarity, the interrogation of a two-dimensional plane with multiple pushing locations (the axial/azimuthal plane—see FIG. 7 where transducer array 32 is positioned over a target region represented as a cube containing a region of varying stiffness 31) has been described. In other embodiments, methods can be carried out in a manner that includes the interrogation of a three-dimensional volume. This may be accomplished in a variety of ways. According to examples illustrated in FIG. 8, where a transducer array 42 is positioned over a target region represented as a square containing a region of varying stiffness 41, and is translated from a first position as shown by 42 to a second position shown by 42', one can use the existing planar system and translate the transducer in the elevation dimension to sequentially interrogate a series of planes comprising a three-dimensional volume. According to examples illustrated in FIG. 9, where transducer array 52 is positioned over a target region represented as a square containing a region of varying stiffness 51, one can use a two-dimensional transducer array (i.e. one that has several rows of elements), and keep the transducer in one location, and steer the beam (represented as lines within the cube) to interrogate a three-dimensional sector of the target region.

When using the ultrasound transducer array to either generate the high intensity pushing pulses, or the displacement tracking pulses, a set of multiple elements may be used to generate each line. The set of elements that is used can either comprise all of the elements in the transducer array, or include only a subset of the elements. The specific elements that are active for each transmit pulse may be determined by the desired focal depth, resolution, and depth of field for each line. According to some embodiments, the pushing beams can be tightly focused, therefore a fairly large number of elements can be used to generate each pushing beam.

The spatial peak temporal average intensities required to generate detectable displacements in tissue vary depending upon the tissue acoustic and mechanical characteristics. They can be from 10 W/cm$^2$ to 1000 W/cm$^2$, with higher intensities being associated with better Signal-to-Noise-Ratios (SNRs). A trade-off may be found, however, between increasing intensities and the potential for tissue heating. Intensities may be used in the 100 to 400 W/cm$^2$ range to reduce tissue heating and maintain a sufficient degree of intensity. These values may be higher than those used for diagnostic imaging (0.72 W/cm$^2$), and lower than those used for HIFU (High Intensity Focused Ultrasound) imaging (1000 W/cm$^2$). Given the short application time in a single location, (i.e. 15 milliseconds), the required intensities should not pose a significant risk to the patient.

In the method implementation described herein, the high intensity acoustic energy can be applied by using a series of multiple, relatively short duty cycle pulses (i.e. 40 pulses, each 10 microseconds long, applied over a time period of 10 milliseconds). The method can also be accomplished by delivering the same amount of acoustic energy in a much shorter time period using a single long pulse (i.e. 1 pulse, 0.4 milliseconds long). A sufficient amount of acoustic energy may be delivered to the tissue to achieve a given displacement. The amount of energy to achieve a given displacement can be accomplished using any number of pulsing regimes. One mode of implementation is to use a single, long pulse (i.e. 0.5 milliseconds), to achieve the initial displacement, and then to intersperse some of the shorter duty cycle (i.e. 10 microseconds) high intensity pulses with the tracking pulses to hold the tissue in its displaced location while tracking. This may reduce the amount of time required at each pushing location, and thus reduce the potential for tissue heating, while at the same time still achieving the desired tissue displacements. The use of a single, long pulse may, however, require additional system modifications. It may, for example, require the addition of heat sinking capabilities to the transducer, as well as modification of a standard power supply to allow the generation of longer pulses.

Figure 10:
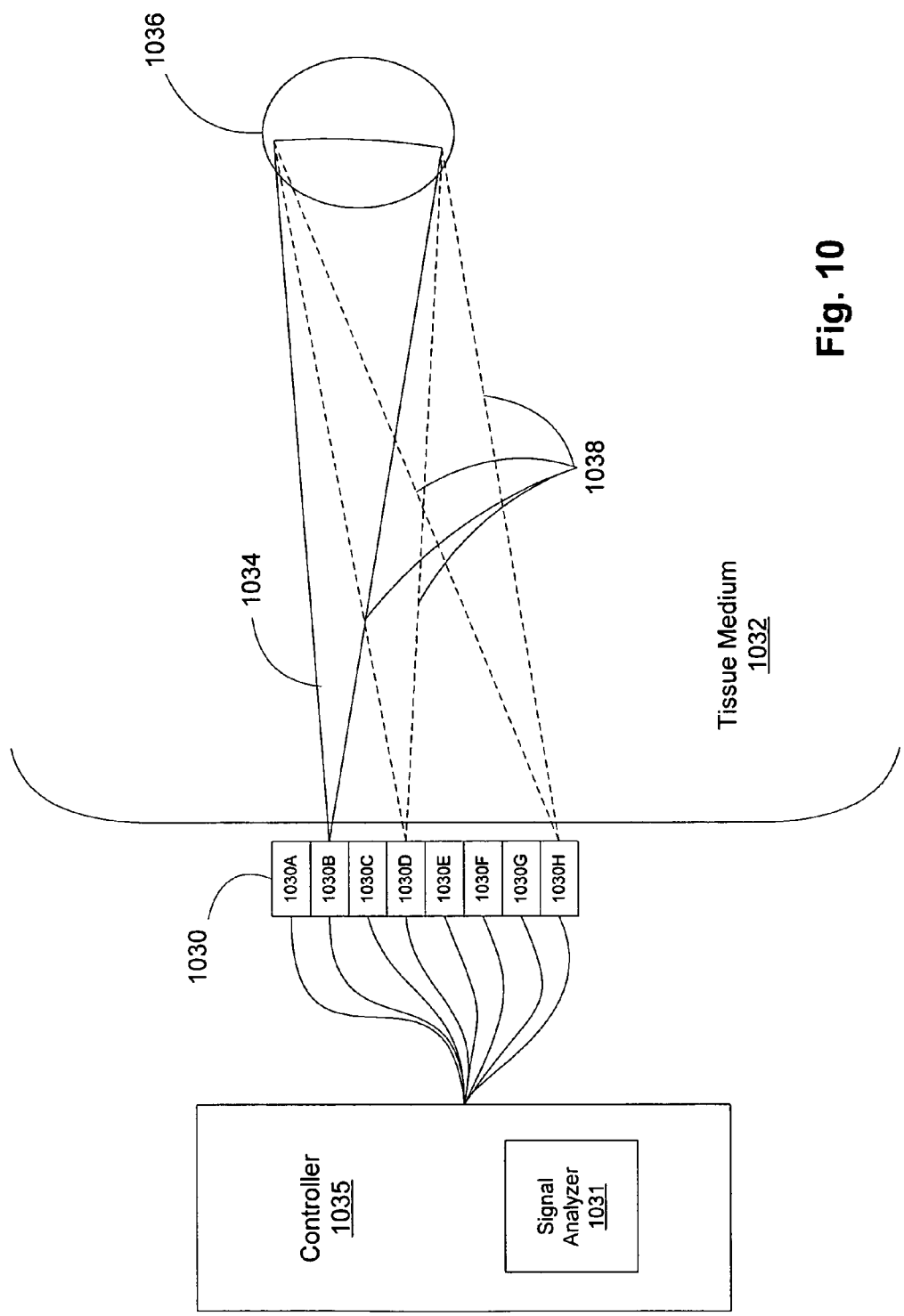
FIG. 10 is a schematic diagram of systems using parallel receive mode processing according to embodiments of the present invention.

In some embodiments, tissue heating may be reduced by parallel processing techniques, as described in more detail with respect to FIG. 10.

The displacement data from each pushing location is combined to form a single image. In order to achieve a uniform image, normalization may be useful. There are three features may benefit from normalization: 1) attenuation, 2) pushing function shape and non-uniformity, and 3) time of acquisition of tracking lines. Each of these features may be normalized out of the image, such that a Remote Palpation image of a homogeneous region of tissue will appear uniform.

While embodiments according to the invention have been described with reference to lesion identification and characterization, some embodiments will also find use in any area where information about the varying mechanical properties of tissue or any other material subject to ultrasonography may be useful. Some examples include: 1) the characterization of arterial stiffness, which can be indicative of the degree of atherosclerotic disease, 2) the assessment of muscle tone, which is of importance in determining the course of treatment for female pelvic floor complications, and 3) assessing the stiffness of kidneys, which can be indicative of the viability of kidney transplants.

Receive Mode Parallel Processing

As described above, receive mode parallel processing can be used to interrogate blood vessels. It will be understood that in some embodiments receive mode parallel processing can also be used independent of the interrogation of blood vessels. In particular, embodiments according to the present invention that can receive ultrasound tracking signals from locations in a target region are shown in FIG. 10. A controller 1035 having a signal analyzer 1031 is operatively connected to an ultrasound transducer array 1030. The transducer array 1030 includes transducer array elements 1030A-1030H that can deliver ultrasound pulses to a tissue medium 1032 to interrogate a target region 1036. Reflected ultrasound signals from the tissue medium 1032 can be received by the array elements 1030A-1030H.

As illustrated in FIG. 10, an exemplary ultrasound pulse 1034 that is de-focused with respect to the target region 1036 propagates from array element 1030B through the tissue medium 1032 to the target region 1036. Portions of the ultrasound pulse 1034 can be reflected towards the transducer array 1030. Reflected ultrasound waves can be received from a plurality of directions 1038 by the transducer array 1030, as shown, by array elements 1030D and 1030H. It should be understood that pulses, such as pulse 1034, can be delivered by any of the array elements 1030A-1030H and that reflected waves can be received by any of the array elements 1030A-1030H.

The signal analyzer 1031 can analyze the various signals received by the array elements 1030A-1030H. According to some embodiments of the present invention, the signal analyzer 1031 can process the signals received by the array elements 1030A-1030H using receive mode parallel processing techniques. For example, the signal analyzer 1031 can sum the signals received by array elements 1030A-1030H using a focal delay so that the various signals will be in phase with one another. Examples of receive mode parallel processing techniques are shown in U.S. Pat. No. 5,544,655 to Daigle, U.S. Pat. No. 5,718,230 to Chapman et al., and U.S. Pat. No. 5,685,308 to Wright et al., the disclosures of which are hereby incorporated by reference in their entirety.

Figure 11:
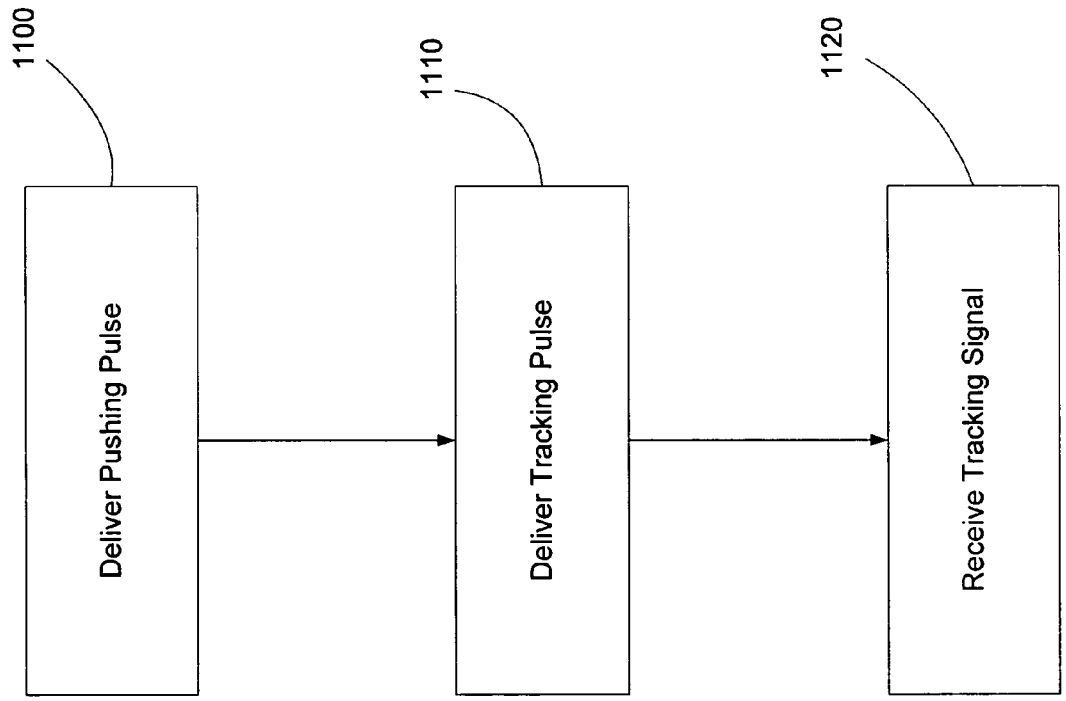
FIG. 11 is a flow chart illustrating operations according to embodiments of the present invention.

According to some embodiments of the present invention, ultrasound signals can be received from locations in the target region, such as is shown in FIG. 10. The received signals can be summed using a focal delay or phase adjustment. For example, as shown in FIG. 11, a pushing pulse can be delivered from an ultrasound transducer array, such as array 1030, to a target region within a medium to displace the target region to a displaced position (Block 1100). A tracking pulse can then be delivered from the ultrasound transducer array to the target region (Block 1110). A tracking signal can be received by the transducer array responsive to the tracking pulse from locations in the target region (Block 1120). By using receive mode parallel processing techniques to analyze the tracking signals from locations in the target region, such as by using multiple sums of differently focused delayed signals, additional information can be gathered for each pushing pulse so that the frame rate can be increased. In addition, fewer pushing pulses may be used, which can result in reduced tissue heating.

Blood Vessel Interrogation and/or Evaluation

Figure 12:
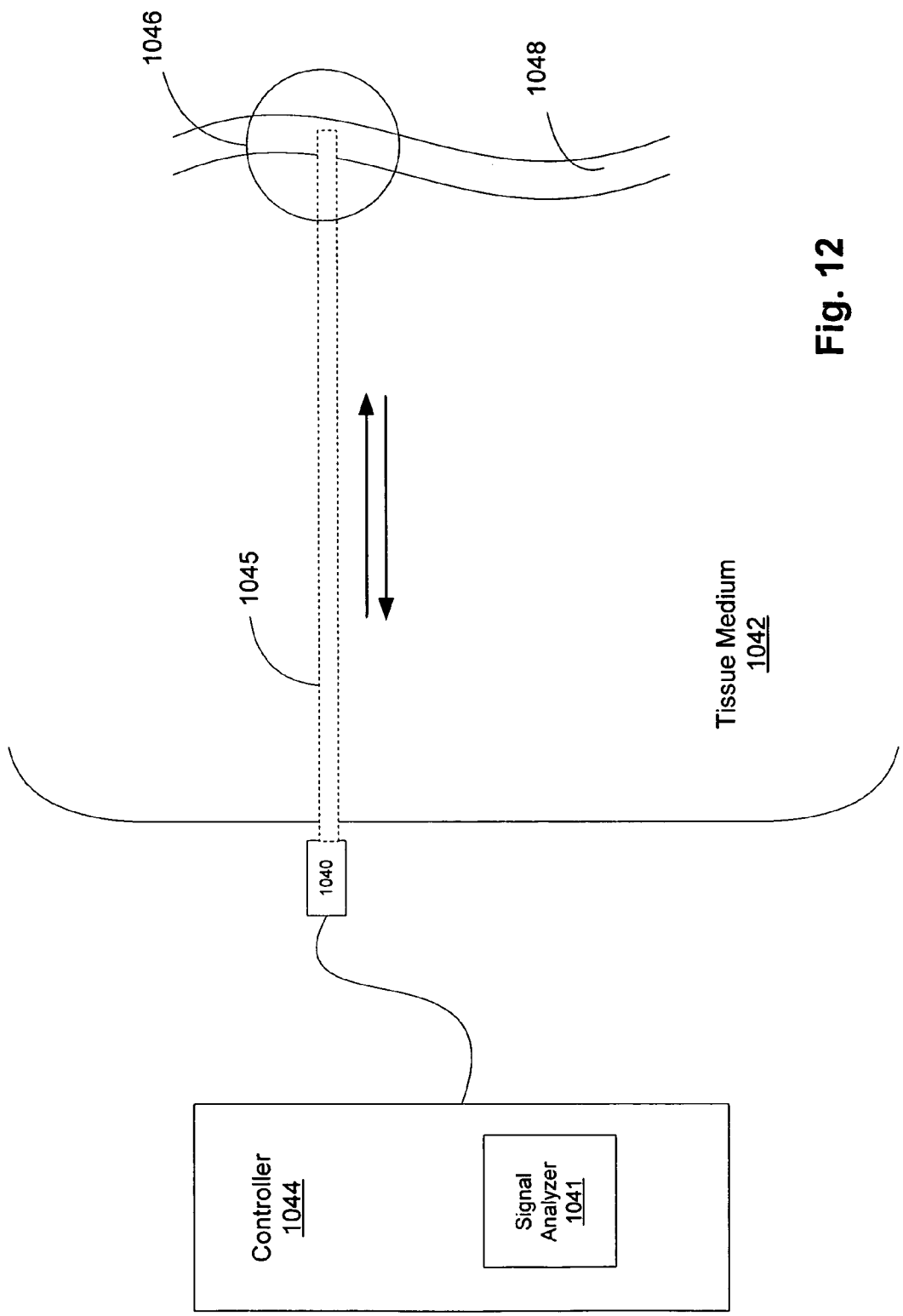
FIG. 12 is a schematic diagram of systems for interrogating blood vessels and cardiac tissue according to embodiments of the present invention.

As described above, receive mode parallel processing can be used to interrogate blood vessels using ultrasound interrogation techniques. It will be understood that blood vessels can be interrogated independently of receive mode parallel processing techniques. In particular, further embodiments according to the present invention for interrogating a target region 1046 including a blood vessel 1048 are shown in FIG. 12. A controller 1044 including a signal analyzer 1041 is connected to an ultrasound transducer 1040. The controller 1044 can provide the transducer 1040 to deliver a pulse 1045 along a propagation path to a target region 1046 in a tissue medium 1042. A reflected wave can travel along the propagation path to be received by the transducer 1040. The pulses can include ultrasound "tracking" or "pushing" pulses as described herein, and the reflected wave can be a tracking signal. Although a single transducer 1040 is shown in FIG. 12, a transducer array could also be used and/or receive mode parallel processing techniques may be employed.

Accordingly, embodiments of the invention may be useful to determine blood vessel health in arterial and veinal vessels, including the popliteal artery and coronary artery, as well as heart tissue, and in particular, in the carotid artery of a subject by detecting values associated with mechanical properties of a blood vessel or cardiac tissue. For clarity and ease of presentation, embodiments of the invention may be described herein with reference to blood vessels and/or cardiac tissue. However, embodiments of the invention may be carried out on blood vessels, cardiac tissue and tissue surrounding and/or adjacent a vessel or cardiac tissue. Thus, it is understood that a detected mechanical property of a blood vessel or cardiac tissue can include a detected property of the tissue surrounding the vessel wall or cardiac tissue.

Advances in imaging and diagnostic techniques, including the techniques described herein, may be used to measure certain mechanical properties of a blood vessel wall. However, in some cases, it may be difficult to obtain absolute measurements of stiffness using such techniques, which may indicate increased stiffness of a region only relative to surrounding tissue. Furthermore, even if absolute measurements of stiffness were easily obtained, it may be difficult to define a clinical standard for correlating such a stiffness measurement to vascular health. Each individual may have a different baseline healthy level of vessel wall stiffness. An amount of stiffness that may be healthy in one individual could be an indication of disease in another individual, for example, based on age or genetic disposition.

Numerous variations and implementations of the instant invention will be apparent to those skilled in the art. A mechanical property of a vessel wall can be detected using methods and systems known to those of skill in the art, including detection methods and systems discussed herein and/or disclosed in U.S. Pat. No. 6,371,912. As used herein, the term "mechanical property" includes any property or characteristic that can be indicative of a mechanical property. For example, stiffness is a mechanical property that can be a function of the material that forms an object as well as the shape of the object and the tissue surrounding the object. Characteristics that can be measured to describe mechanical properties include recovery times, displacement subsequent to forced movement, time to peak displacement, viscosity, and stiffness. In some embodiments, mechanical properties can be measured by relative measurements under similar conditions, and therefore, an absolute measurement of the mechanical property may be unnecessary to characterize the property. For example, the reaction or vibrations of a material due to the application of an ultrasound pulse can indicate mechanical properties of the material.

Figure 13:
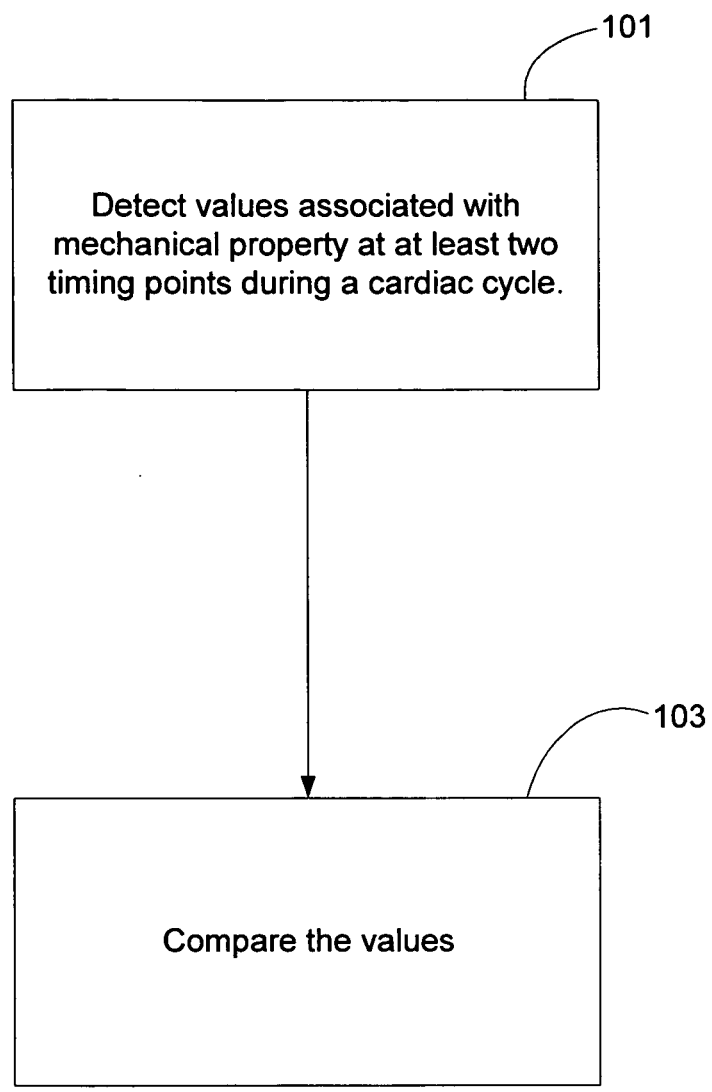
FIGS. 13-16 are flow charts illustrating various operations according to embodiments of the present invention.

With reference to FIG. 13, a value associated with a mechanical property of a vessel wall and/or cardiac tissue is detected at at least two timing points during the cardiac cycle of a subject (Block 101). The value of the mechanical property can be a measurement of stiffness, viscosity, recovery time constant, displacement, time to peak displacement, or a dynamic response to radiation force excitation. The mechanical property can be detected at a single point in time or over a period of time, typically about 5 ms to about 10 ms. For example, an observed response to an excitation pulse can be observed over a period of time to determine a maximum displacement and/or a time to peak displacement. Examples of timing points include one point at a relaxed point in the cardiac cycle, and another point at an expanded point, or a point during systole and a point during diastole. The values associated with the mechanical properties at the two timing points are compared to evaluate the blood vessel and/or cardiac tissue, such as to determine a measure of vessel and/or cardiac health or diagnose a medical condition (Block 103).

The comparison can be any qualitative or quantitative comparison and can be visual or mathematical. The comparison can be carried out by visually observing a difference in a mechanical property in an ultrasound image of the vessel wall or quantitatively detecting a change in the detected mechanical property. The comparison may include experimentally determined evaluation standards for health and disease that can be determined by a statistical evaluation of a representative population. Evaluation standards may be established to account for differences based on sex, age, smoking and other factors. The comparison can include normalizing the evaluation based on vessel distensibility, blood pressure or other physiologic characteristics such as sex, age, smoking, and similar factors. The evaluation standards can include a threshold value, above or below which is deemed unhealthy or a graduated scale for determining a range of relative health. As used herein, a "point" can be a one-, two-, or three-dimensional area ranging from an infinitesimally small point to an area with dimensions on the order of microns, millimeters, centimeters, or more. In some embodiments, a "point" can be an isolated region, such as a tissue layer in a blood vessel or cardiac area or a focal lesion.

Figure 14:
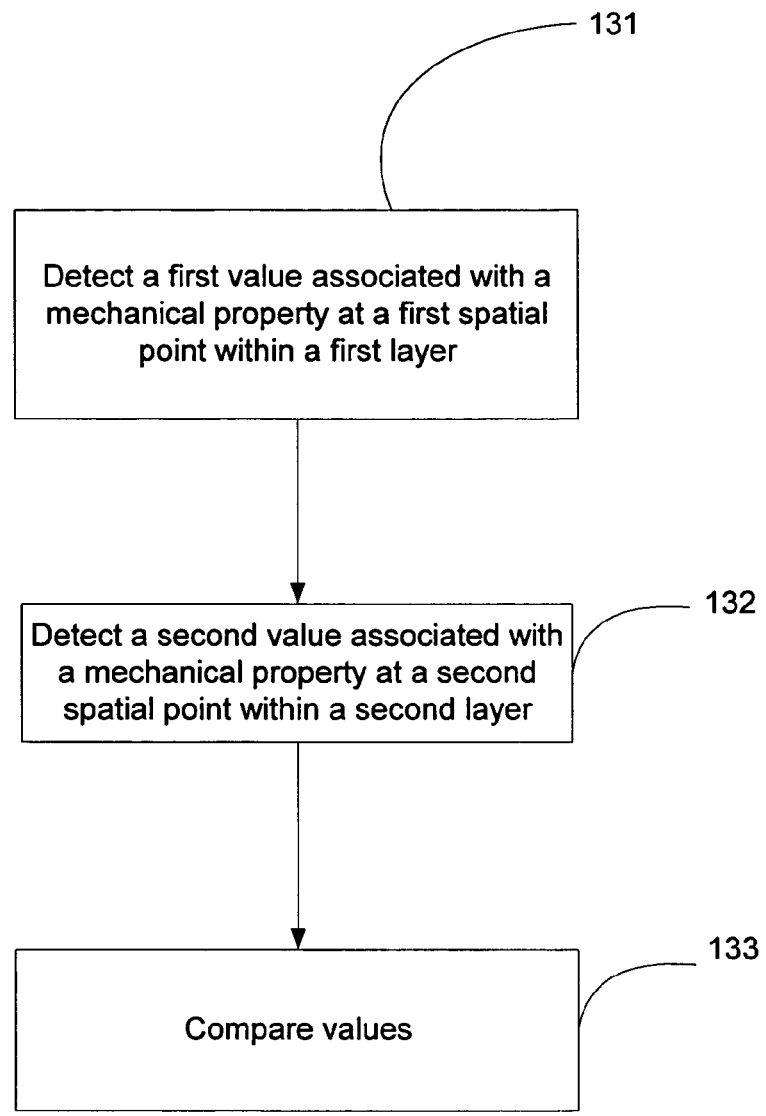

In other embodiments as shown in FIG. 14, a first value associated with a mechanical property of a vessel wall and/or cardiac tissue can be detected at a first spatial point within a first layer of a vessel wall (Block 131), and a second value associated with a mechanical property at a second spatial point within another tissue layer such as a second vessel wall layer (Block 132). The layers may include various tissues within the heart or vessel wall layers such as focal lesions, the inner endothelium layer, the media smooth muscle layer, and the outer adventita connective tissue layer. The detected mechanical property is compared at the two spatial points to evaluate the blood vessel and/or cardiac tissue (Block 133). The spatial points can include areas of vessel wall, including focal lesions, and/or cardiac tissue. Preferably, the two tissue layers are the media and adventita layers.

Without wishing to be bound by theory, it is currently believed that the relative mechanical properties of diseased vessel tissue during various points in the cardiac cycle or at various points within different vessel wall layers may be used to measure blood vessel health. Mechanical properties at a single spatial or temporal point may provide some indication of blood vessel health, however, the healthy baseline of a mechanical property such as stiffness, recovery time constants, viscosity, or displacement measurements may vary based on age, gender, ethnicity, location in the body, or even randomly between individuals. Thus, comparing relative mechanical properties during various points in the cardiac cycle as the vessels expand and contract or between vessel wall layers may provide a measurement of vascular health. Such relative measurements in a subject may account for varying individual characteristics. It is currently believed that a greater relative change in a mechanical property such as stiffness indicates lesser arterial health over smaller relative changes.

As discussed briefly above, examples of detected mechanical properties include a dynamic response to radiation force excitation, a measurement of stiffness, a measurement of a recovery time constant, a measurement of viscosity, a measurement of time to peak displacement and/or a measurement of displacement. Mechanical properties can be derived measurements based on observed responses of tissue to an excitation force. Various parameters can be selected from the observed responses as a detected mechanical property without necessitating an absolute measurement or direct measurement of a mechanical property. For example, mechanical properties can be determined from an evaluation of the dynamic response of tissue to radiation excitation forces. The measurement can be made at a single point in time or over a period of time (typically about 5 ms to about 10 ms), for example, to determine the time to peak displacement. The mechanical property of the vessel wall can be detected at one point during systole and at another point during diastole of the cardiac cycle. It is believed that detection of the mechanical property during systole and diastole can maximize the difference between the mechanical property at the two points, thus increasing the sensitivity of a measurement, because measured difference in the detected mechanical property is between a relaxed blood vessel wall and an expanded vessel wall.

Figure 15:
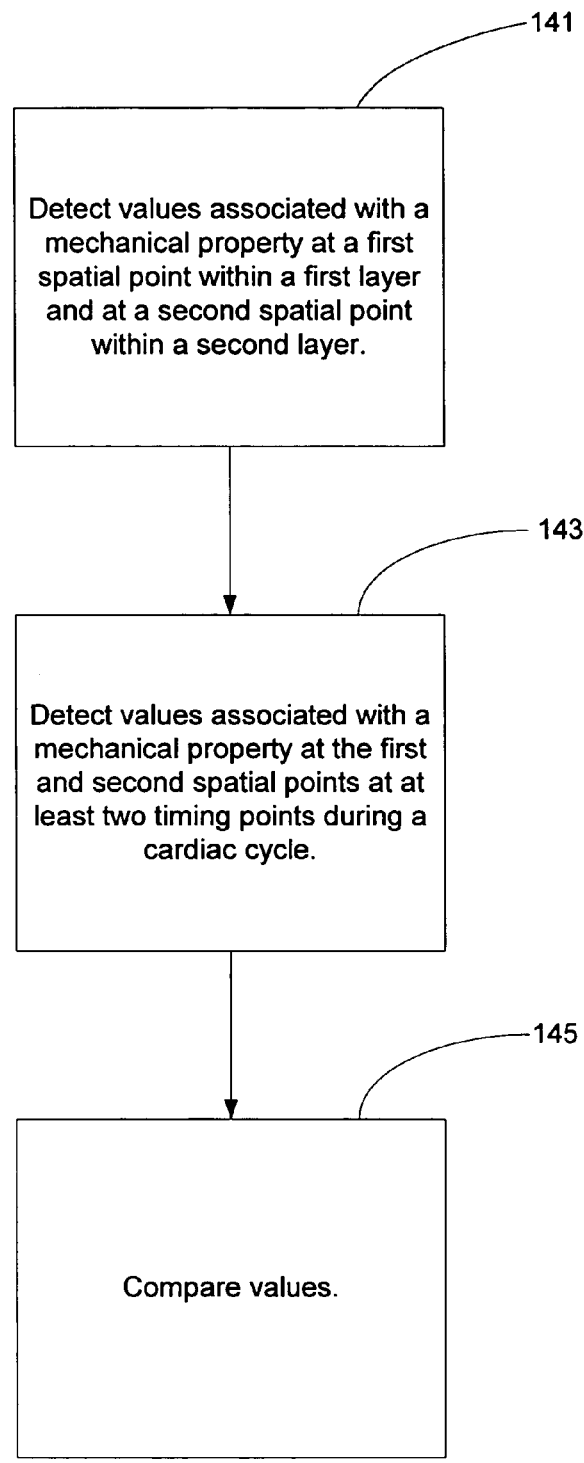

With reference to FIG. 15, further embodiments include detecting a value of a mechanical property of a vessel wall and/or cardiac tissue at two spatial points within two layers, such as two cardiac or vessel wall layers (Block 141). The value of the mechanical property can be detected at the two spatial points at at least two timing points during the cardiac cycle (Block 143). The detected values of the mechanical property at the two spatial points and at the two timing points may then be compared to evaluate the blood vessel and/or cardiac tissue (Block 145). In some embodiments, one mechanical property measurement is made during systole of the cardiac cycle and another mechanical property measurement is made during diastole of the cardiac cycle.

The mechanical property can be detected by methods and systems known to those of skill in the art capable of detecting mechanical properties of vessels as described herein, including remote palpation, ARFI, and receive mode parallel processing ultrasound techniques. For example, systems may be provided for measuring the mechanical property multiple times or at multiple spatial points using ultrasound measurements of the blood vessel wall and comparing those measurements to evaluate blood vessels.

For example, with reference to FIG. 12, beam sequences, which can be delivered by transducer 1040, can be repeated throughout the cardiac cycle. The controller 1044 can be configured to gate the timing of the radiation force interrogations delivered by the transducer 1040 with an electrocardiogram. Other ways of timing the radiation force interrogations or determining the timing of the collected data can be used. For example, displacement maps can be generated over a period of time, and the timing of the map with respect to cardiac cycle can be determined from the map itself. The radiation force interrogations can also be gated with a blood pressure measurement to determine the timing of the cardiac cycle. Data can be collected by the signal analyzer 1041 at specific, predetermined points during the cardiac cycle. Multiple locations along the vessel wall and/or cardiac tissue, including the surrounding tissue, can be evaluated, either using simultaneous measurements or by moving the transducer to evaluate different locations. Data can also be collected by the signal analyzer 1041 throughout a series of closely spaced or continuous measurement during the cardiac cycle. Thus, the entire cardiac cycle can be observed.

Displacement magnitude is generally inversely proportional to local tissue stiffness and, in some embodiments, may be on the order of ten microns. The transient shear wave velocity and shear wave attenuation are also related to the tissue mechanical properties. The volume of tissue to which radiation force is applied can be determined by the focal characteristics of the transmitting transducer. Comparison of detected mechanical properties can be accomplished in various ways. For example, the ratio of matched parameters such as maximum displacement or recovery time constant can be compared. Such comparisons may be made at various points in the cardiac cycle, such as at systole and diastole, and/or with respect to measurements at different blood vessel wall layers or over a period of time.

Figure 16:
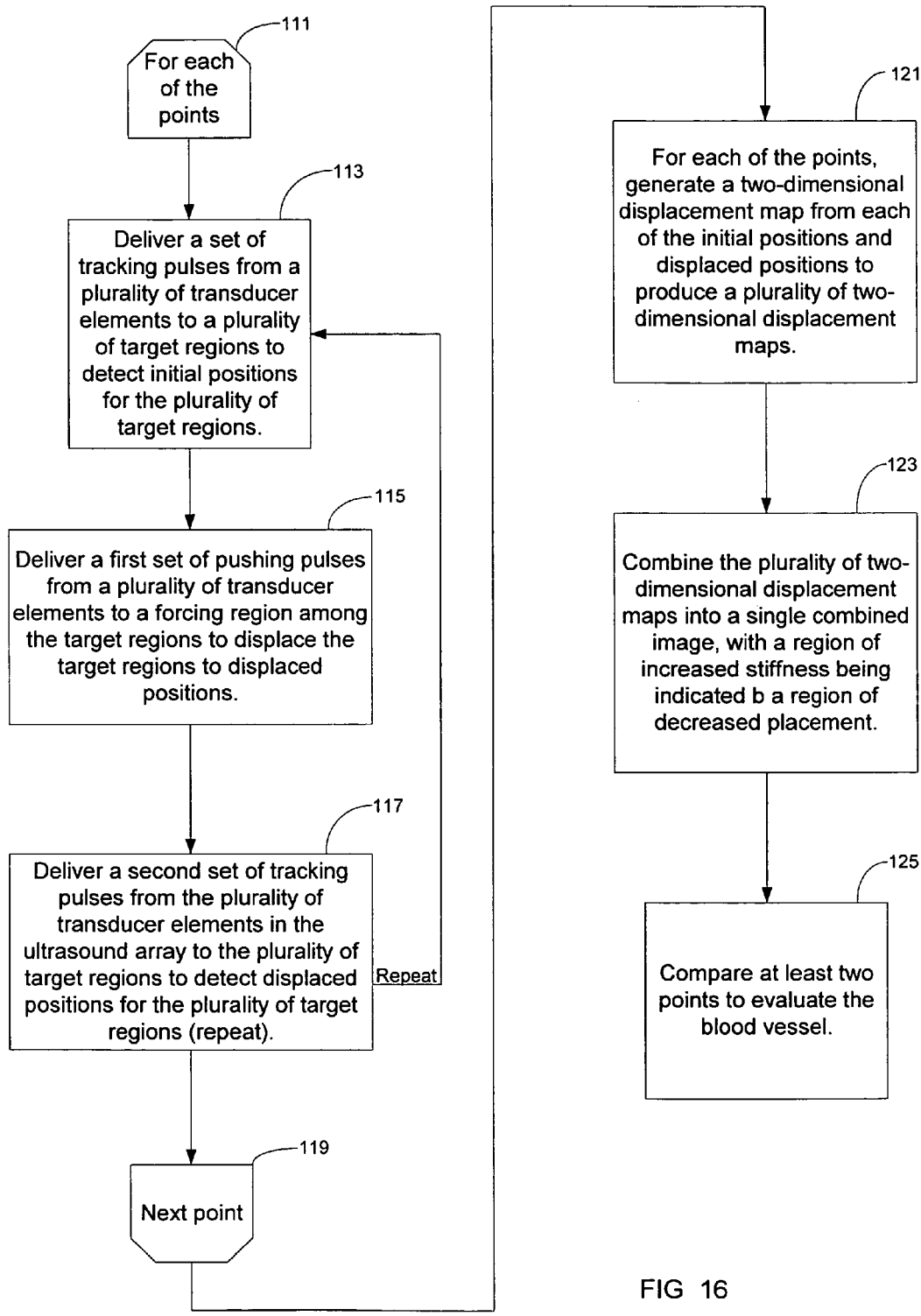

FIG. 16 illustrates operation of the system of FIG. 12 in further detail. As seen in FIG. 16, for each of the spatial or timing points (Block 111) a set of one or more tracking pulses are delivered from a plurality of transducer elements in an ultrasound transducer array, such as transducer array 1040 in FIG. 12, to a plurality of target regions in a two-dimensional plane intersecting the vessel wall to detect initial positions for target regions (Block 113). A first set of one or more pushing pulses is delivered from the transducer array 1040 to a forcing region among the target regions to displace the target regions (Block 115). A second set of one or more tracking pulses is delivered from the transducer array 1040 to the target regions to detect displaced positions (Block 117). The step of Block 117 can be repeated for a single set of pushing pulses over a period of time, such as between about 5 ms and about 10 ms. The repetition of the tracking pulses in the step of Block 117 can be used to observe a reaction over a period of time, for example, to determine displacement over time and/or the time to peak displacement for an interrogation pulse. In addition or alternatively, the steps of Block 113, Block 115, and Block 117 may be repeated at the same point. The steps of Block 113, Block 115, and Block 117 may be repeated one or more times for the next point (Block 119). The points at which the mechanical property is measured may be timing points at different points during the cardiac cycle and/or spatial points at different positions within blood vessel walls. In some embodiments, the steps of Block 113, Block 115, and Block 117 can be repeated in a series of cycles, with the pushing pulses being delivered to a different forcing region and different target regions during each of the cycles.

For each of the points, a two-dimensional displacement maps from each of the initial positions and displaced positions can be generated to produce a plurality of two-dimensional displacement maps (Block 121). The plurality of two-dimensional displacement maps can be made over time to show characteristics such as displacement over time. The plurality of two-dimensional displacement maps can be combined into a single image for each point, with a region of increased stiffness being indicated by a region of decreased displacement (Block 123). The images can be combined into a single parametric image, for example, isolating one or more evaluation criteria. Two or more spatial and/or timing points can be compared to evaluate the blood vessel and/or cardiac tissue (Block 125). Images may also be made in one or three dimensions.

The operations shown in FIG. 16 can be used to detect mechanical properties for both timing and spatial points at various times during the cardiac cycle and/or within two or more tissue layers, such as cardiac tissue layers and/or vessel wall layers.

Other imaging techniques and non-imaging data analysis techniques known to those of skill in the art may be used to compare spatial and timing points at which a mechanical property is detected.

Figure 17:
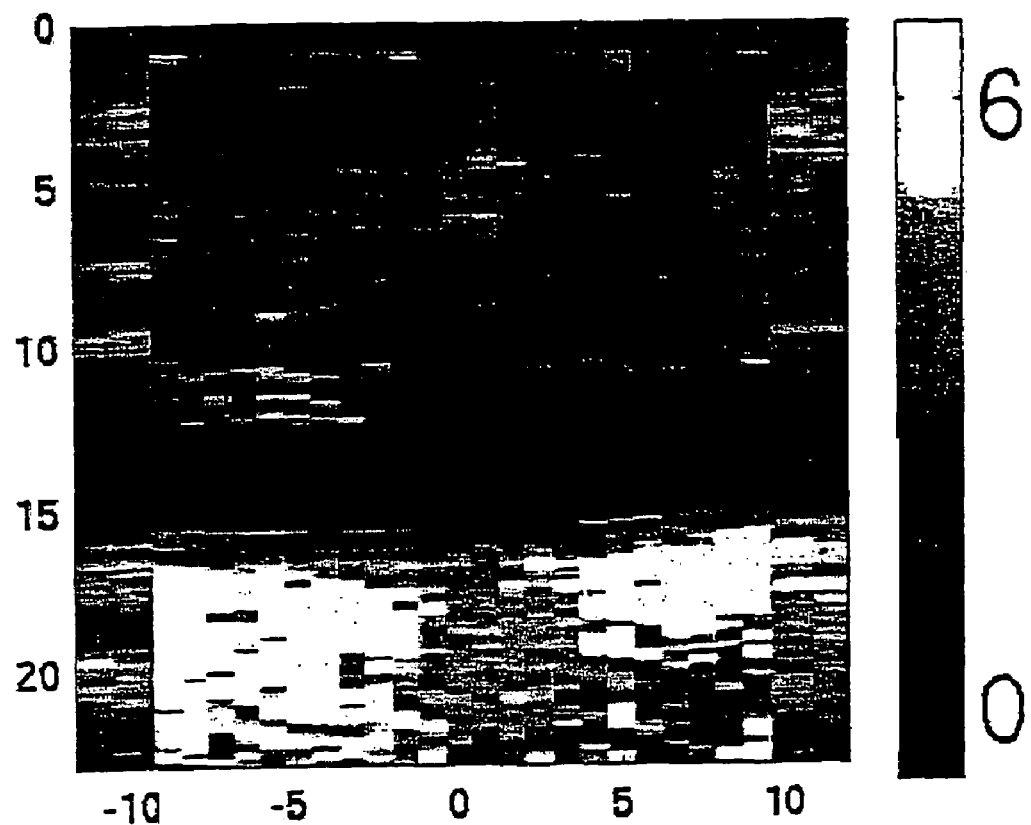
FIGS. 17 and 18 are images obtained using systems according to embodiments of the invention.
Figure 18:
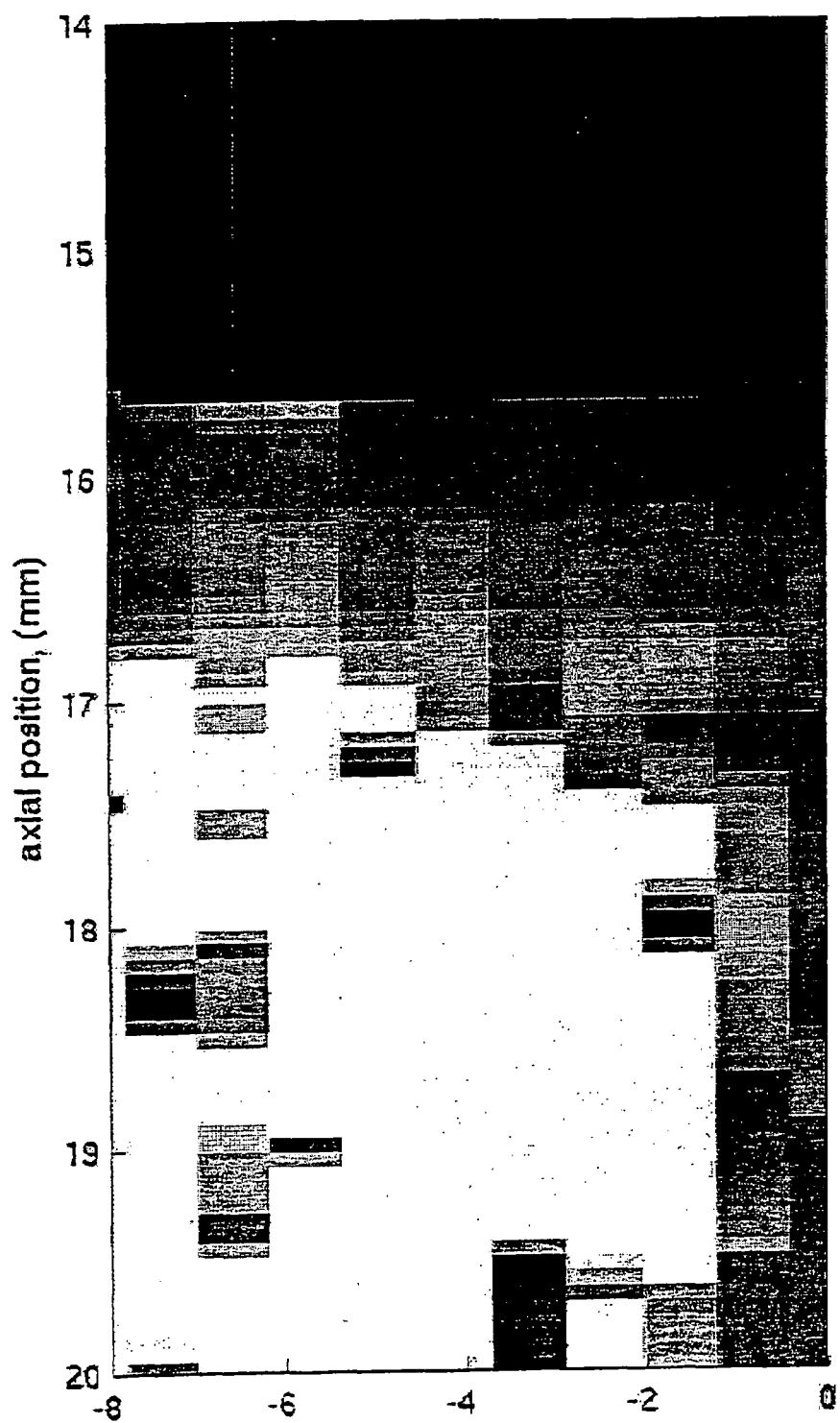
Figure 19:
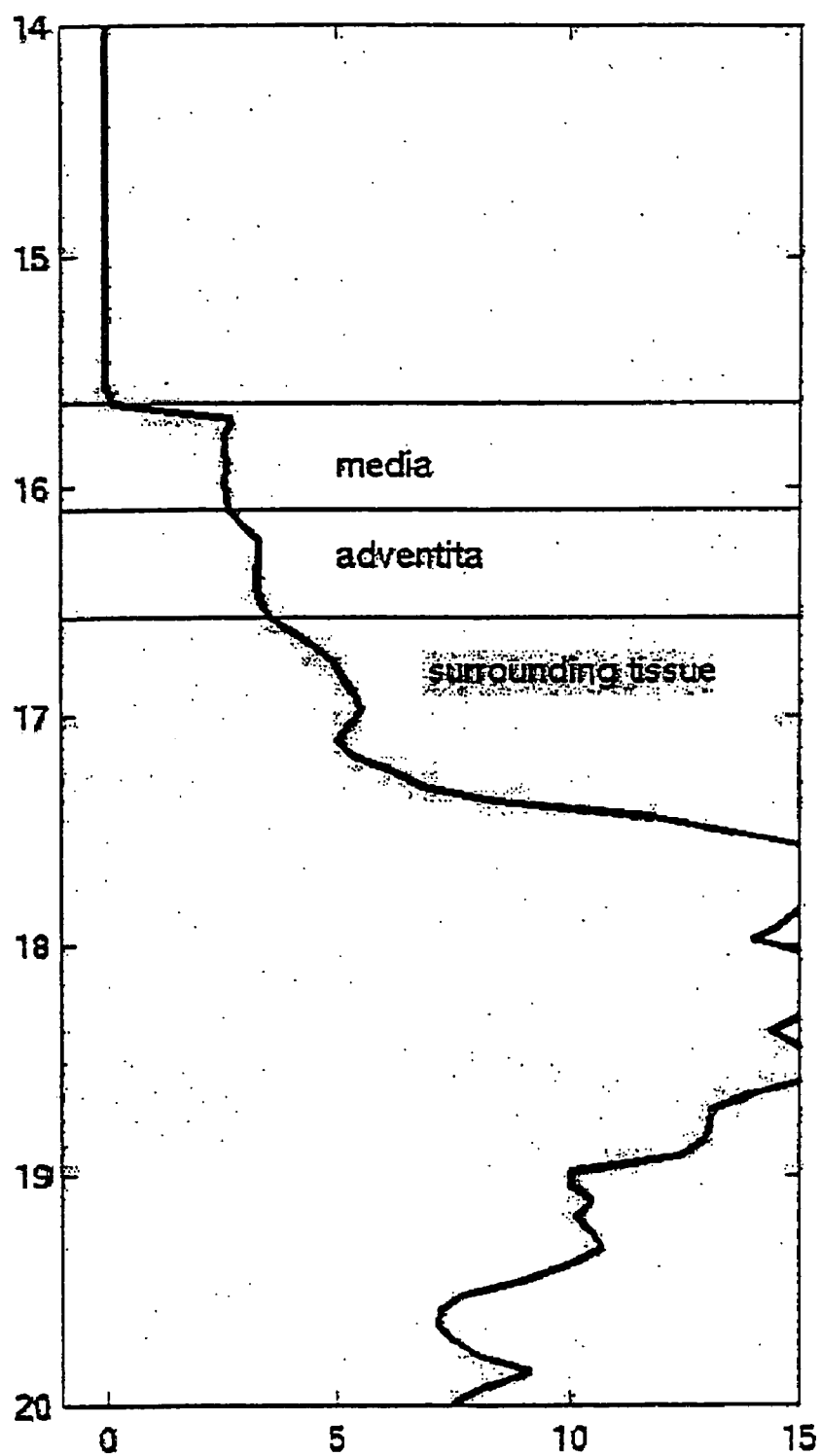
FIG. 19 is a displacement value plot obtained from the ultrasound measurements of FIGS. 17 and 18 according to embodiments of the present invention.

FIGS. 17 and 18 are images produced using ultrasound techniques described in U.S. Pat. No. 6,371,912. FIG. 17 is a displacement image obtained by operations shown in FIG. 16 of an in vivo carotid obtained during diastole, which shows a delineation of the posterior vessel wall. FIG. 18 is a magnified illustration of the image in FIG. 17. FIG. 19 illustrates the displacement value (plotted on the horizontal axis) as a function of position from the data used to produce FIGS. 17 and 18. The images in FIGS. 17, 18, and 19 were generated using displacement data 0.1 msec after radiation force application.

While the present invention may be used to detect regions of varying stiffness (i.e., increased or decreased elastic modulus) in any type of medium, the medium is in a preferred embodiment a biological tissue such as breast tissue in a living subject, where the regions of varying stiffness to be detected are tumors.

The invention may be carried out on human subjects for diagnostic or prognostic purposes, and may be carried out on animal subjects such as dogs and cats for veterinary purposes.

Circuits and devices described herein may be implemented as general or special purpose hardware devices, as software running on or programmed into general or special purpose hardware devices, or as combinations thereof.

Numerous variations and implementations of the instant invention will be apparent to those skilled in the art. Conventional ultrasound apparatus is known, and is described in, for example, U.S. Pat. No. 5,487,387 to Trahey et al.; U.S. Pat. No. 5,810,731 to Sarvazyan and Rudenko; U.S. Pat. No. 5,921,928 to Greenleaf et al.; M. Fatemi and J. Greenleaf, Ultrasound-stimulated vibro-acoustic spectrography, *Science*, 280:82-85, (1998); K. Nightingale, *Ultrasonic Generation and Detection of Acoustic Streaming to Differentiate Between Fluid-Filled and Solid Lesions in the Breast*, Ph.D. thesis, Duke University, 1997; K. Nightingale, R. Nightingale, T. Hall, and G. Trahey, The use of radiation force induced tissue displacements to image stiffness: a feasibility study, 23$^{rd}$ International Symposium on Ultrasonic Imaging and Tissue Characterization, May 27-29, 1998; K. R. Nightingale, P. J. Kornguth, S. M. Breit, S. N. Liu, and G. E. Trahey, Utilization of acoustic streaming to classify breast lesions in vivo, In *Proceedings of the 1997 IEEE Ultrasonics Symposium*, pages 1419-1422, 1997; K. R. Nightingale, R. W. Nightingale, M. L. Palmeri, and G. E. Trahey, Finite element analysis of radiation force induced tissue motion with experimental validation, In *Proceedings of the 1999 IEEE Ultrasonics Symposium, page in press*, 1999; A. Sarvazyan, O. Rudenko, S. Swanson, J. Fowlkes, and S. Emelianov, Shear wave elasticity imaging: A new ultrasonic technology of medical diagnostics, *Ultrasound Med. Biol.* 24:9 1419-1435 (1998); T. Sugimoto, S. Ueha, and K. Itoh, Tissue hardness measurement using the radiation force of focused ultrasound, In *Proceedings of the 1990 Ultrasonics Symposium*, pages 1377-1380, 1990; and W. Walker, Internal deformation of a uniform elastic solid by acoustic radiation force, *J. Acoust. Soc. Am.*, 105:4 2508-2518 (1999). The disclosures of these references are to be incorporated herein by reference in their entirety for their teaching of various elements and features that may be used to implement and carry out the invention described herein.

The foregoing is illustrative of the present invention, and is not to be construed as limiting thereof. The invention is described by the following claims, with equivalents of the claims to be included therein.

We claim:

1. An ultrasound method comprising:
  delivering a pushing pulse for between about 0.025 to about 10 milliseconds from an ultrasound transducer array having a plurality of elements to a target region within a medium to displace the target region to a displaced position;
  delivering a tracking pulse from the ultrasound transducer array to the target region; and
  receiving a plurality of tracking signals from locations in the target region, each tracking signal being responsive to the tracking pulse, and forming parallel beamformed signals from the plurality of tracking signals.

2. A method according to claim 1 wherein the plurality of tracking signals detects the displaced position of the target region.

3. A method according to claim 1 further comprising
  delivering an initial tracking pulse from the ultrasound transducer array to the target region prior to the pushing pulse; and
  receiving an initial tracking signal responsive to the tracking pulse in the target region to detect an initial position for the target region.

4. A method according to claim 3 wherein the tracking signals comprise multiple sums of differently focused delayed signals received at each of the plurality of elements in the ultrasound transducer array.

5. A method according to claim 3 wherein:
  delivering a tracking pulse comprises delivering the tracking pulse at a first intensity level; and
  delivering a pushing pulse comprises delivering the pushing pulse at a second intensity level that is greater than the first intensity level.

6. A method according to claim 5 wherein the second intensity level is a range between about 1.0 W/cm2 and about 10,000.0 W/cm2.

7. A method according to claim 5 wherein the first intensity level is less than about 1.0 W/cm2.

8. A method according to claim 1 wherein the tracking pulses comprise a de-focused beam with respect to the target region.

9. A method according to claim 1 wherein transmitting a tracking pulse and receiving a plurality of tracking signals are repeated for a single pushing pulse.

10. A method according to claim 1 wherein the ultrasound transducer array comprises a one dimensional ultrasound transducer array.

11. A method according to claim 1 wherein the ultrasound transducer array comprises a two dimensional ultrasound transducer array.

12. A method according to claim 1 further comprising detecting a region of greater stiffness relative to other regions indicated by a region of decreased displacement relative to other regions.

13. A method according to claim 12 wherein the medium comprises a biological tissue, and the region of greater stiffness is a tumor.

14. A method according to claim 13 wherein the tissue comprises breast tissue.

15. A method according to claim 12 wherein the medium comprises a blood vessel and the region of greater stiffness comprises a hardened blood vessel.

16. A method according to claim 12 wherein the medium comprises muscle tissue and the region of greater stiffness comprises muscle tissue with greater muscle tone relative to other regions.

17. A method according to claim 1 further comprising detecting a region of lesser stiffness relative to other regions indicated by a region of greater displacement relative to other regions.

18. A method according to claim 1 further comprising displaying an image based on a relative amplitude of the displaced position at a plurality of spatial points.

19. A method according to claim 18 wherein the image comprises a two-dimensional image.

20. A method according to claim 19 wherein the image comprises a three-dimensional image.

21. A method according to claim 1 further comprising precompressing the target region prior to delivering the pushing pulse.

22. A method according to claim 1 further comprising repeating the steps of delivering a tracking pulse and receiving a tracking signal responsive to the tracking pulse after the step of delivering the pushing pulse.

23. An ultrasound method comprising the steps of:
  delivering a first tracking pulse from an ultrasound transducer array to a target region within a medium;
  receiving a first set of tracking signals from locations in the target region responsive to the tracking pulse in the target region at the ultrasound transducer array to detect an initial position for the target region;

delivering a pushing pulse for between about 0.025 to about 10 milliseconds from the ultrasound transducer array to the target region to displace the target region to a displaced position;

delivering a second tracking pulse from the ultrasound transducer array to the target region;

receiving a second set of tracking signals from locations in the target region responsive to the second tracking pulse at the ultrasound transducer array to detect the displaced position of the target region forming parallel beamformed signals from the plurality of tracking signals; and repeating sequentially the delivering a first tracking pulse, receiving a first tracking signal, delivering a pushing pulse, delivering a second tracking pulse, and receiving a second tracking signal to provide a series of cycles, the pushing pulses being delivered to different target regions during the series of cycles providing a plurality of displaced positions.

24. A method according to claim 23 further comprising:
generating a plurality of displacement maps based on a relaxed position in the target region and the plurality of displaced positions; and then
combining the plurality of displacement maps to provide an image.

25. A method according to claim 23 wherein repeating sequentially further comprises delivering the pushing pulses from different transducer elements in the ultrasound transducer array to different target regions during the cycles.

26. A method for evaluating a blood vessel and/or cardiac tissue in a subject comprising:
delivering an acoustic radiation force pulse to a blood vessel and/or cardiac tissue;
detecting a mechanical property of the vessel wall and/or cardiac tissue responsive to the acoustic radiation force pulse to provide at least first and second values associated with the mechanical property at at least two timing points during a cardiac cycle of the subject;
comparing the first and second values and evaluating a blood vessel and/or cardiac tissue in the subject as a result of the value comparison.

27. A method according to claim 26 wherein a target region comprises blood vessel wall and/or cardiac tissue and wherein delivering an acoustic radiation force pulse and detecting a mechanical property comprises:
delivering a first tracking pulse from an ultrasound transducer array having a plurality of elements to a target region within a medium;
receiving a first set of tracking signals from locations in the target region responsive to the tracking pulse in the target region to detect an initial position for the target region;
delivering a pushing pulse from the ultrasound transducer array to the target region to displace the target region to a displaced position;
delivering a second tracking pulse from the ultrasound transducer array to the target region; and
receiving a second set of tracking signals from locations in the target region responsive to the second tracking pulse in the target region to detect the displaced position of the target region.

28. A method according to claim 27 wherein:
delivering the first tracking pulse comprises delivering the first tracking pulse at a first intensity level; and
delivering a pushing pulse comprises delivering the pushing pulse at a second intensity level that is greater than the first intensity level.

29. A method according to claim 28 wherein:
delivering a second tracking pulse comprises delivering the second tracking pulse at the first intensity level.

30. A method according to claim 28 wherein the second intensity level is a range between about 1.0 W/cm2 and about 10,000.0 W/cm2.

31. A method according to claim 28 wherein the first intensity level is less than about 1.0 W/cm2.

32. A method according to claim 27 wherein the step of delivering a pushing pulse comprises delivering the pushing pulse for between about 0.025 to about 10 milliseconds.

33. A method according to claim 27 further comprising generating a displacement map at the two timing points during the cardiac cycle.

34. A method according to claim 27 further comprising:
generating a plurality of two-dimensional displacement maps from a plurality of initial positions and displaced positions for each of the target regions to produce a plurality of two-dimensional displacement maps; and then
combining the plurality of two-dimensional displacement maps into a single combined map, with a region of increased stiffness being indicated by a region of decreased displacement within the combined map.

35. A method according to claim 26 wherein the detected mechanical property comprises a measurement of stiffness.

36. A method according to claim 26 wherein the detected mechanical property comprises a measurement of a recovery time constant.

37. A method according to claim 26 wherein the detected mechanical property comprises a measurement of displacement.

38. A method according to claim 26 wherein the detected mechanical property comprises a measurement of viscosity.

39. A method according to claim 26 wherein the detected mechanical property comprises a measurement of the time for the tissue to reach a peak displacement.

40. A method according to claim 26 wherein the detected mechanical property comprises a measurement of a mechanical property of a blood vessel wall.

41. A method according to claim 26 wherein the detected mechanical property comprises a measurement of a mechanical property of tissue surrounding a vessel wall.

42. A method according to claim 26 further comprising:
for each of the at least two timing points, detecting a mechanical property of at least two layers of the vessel wall and/or cardiac tissue to provide additional values associated with the mechanical property at the at least two layers; and
comparing first and second values and the additional values.

43. A method according to claim 26 wherein detecting the mechanical property comprises:
detecting the mechanical property of a vessel wall and/or cardiac tissue during systole of the cardiac cycle; and
detecting the mechanical property of a vessel wall and/or cardiac tissue during diastole of the cardiac cycle.

44. A method for evaluating a blood vessel and/or cardiac tissue in a subject comprising:
delivering an acoustic radiation force pulse to a blood vessel and/or cardiac tissue;
detecting a first value associated with the mechanical property of a vessel wall and/or cardiac tissue responsive to the acoustic radiation force pulse at a first spatial point within a first layer of the vessel wall and/or cardiac tissue;

detecting a second value associated with the mechanical property at a second spatial point of the vessel wall and/or cardiac tissue within a second layer of the vessel wall and/or cardiac tissue;

comparing the first and second values, and evaluating a blood vessel and/or cardiac tissue in the subject as a result of the value comparison.

45. A method according to claim 44 wherein a target region comprises blood vessel wall and/or cardiac tissue and wherein delivering an acoustic radiation force pulse and detecting a first and/or second value associated with a mechanical property comprises:

delivering a first tracking pulse from an ultrasound transducer array having a plurality of elements to a target region within a medium;

receiving a first set of tracking signals from locations in the target region responsive to the tracking pulse in the target region to detect an initial position for the target region;

delivering a pushing pulse from the ultrasound transducer array to the target region to displace the target region to a displaced position;

delivering a second tracking pulse from the ultrasound transducer array to the target region; and receiving a second set of tracking signals from locations in the target region responsive to the second tracking pulse in the target region to detect the displaced position of the target region.

46. A method according to claim 45 wherein:

delivering a first tracking pulse comprises delivering the first tracking pulse at a first intensity level; and delivering a pushing pulse comprises delivering the pushing pulse at a second intensity level that is greater than the first intensity level.

47. A method according to claim 46 wherein:

delivering a second tracking pulse comprises delivering the second tracking pulse at the first intensity level.

48. A method according to claim 46 wherein the second intensity level is a range between about 1.0 W/cm2 and about 10,000.0 W/cm2.

49. A method according to claim 46 wherein the first intensity level is less than about 1.0 W/cm2.

50. A method according to claim 46 wherein the step of delivering a pushing pulse comprises delivering the pushing pulse for between about 0.025 and about 10 milliseconds.

51. A computer program product for controlling ultrasound signals comprising:

a computer readable medium having computer readable program code embodied therein, the computer readable program code comprising:

computer readable program code configured to deliver a pushing pulse for between about 0.025 to about 10 milliseconds from an ultrasound transducer array having a plurality of elements to a target region within a medium to displace the target region to a displaced position;

computer readable program code configured to deliver a tracking pulse from the ultrasound transducer array to the target region; and computer readable program code configured to receive a plurality of tracking signals from locations in the target region, each tracking signal being responsive to the tracking pulse, and to form parallel beamformed signals from the plurality of tracking signals.

52. A computer readable program product according to claim 51 wherein the tracking signal detects the displaced position of the target region.

53. A computer readable program product according to claim 51 further comprising computer readable program code configured to deliver an initial tracking pulse from the ultrasound transducer array to the target region prior to the pushing pulse;

computer readable program code configured to receive an initial set of tracking signals responsive to the tracking pulse from locations in the target region to detect an initial position for the target region.

54. A computer readable program product according to claim 53 wherein the tracking pulses comprises a de-focused beam with respect to the target region.

55. A computer readable program product according to claim 53 wherein the tracking signals comprise multiple sums of differently focused focal delayed signals received at each of the plurality of elements in the ultrasound transducer array.

56. A computer readable program product according to claim 53 wherein:

the computer readable program code configured to deliver the tracking pulse comprises computer readable program code configured to deliver the tracking pulse at a first intensity level; and the computer readable program code configured to deliver a pushing pulse comprises computer readable program code configured to deliver the pushing pulse at a second intensity level that is greater than the first intensity level.

57. A computer readable program product according to claim 56 wherein:

the computer readable program code configured to deliver an initial tracking pulse comprises computer readable program code configured to deliver the initial tracking pulse at the first intensity level.

58. A computer readable program product according to claim 56 wherein the second intensity level is a range between about 1.0 W/cm2 and about 10,000.0 W/cm2.

59. A computer readable program product according to claim 56 wherein the first intensity level is less than about 1.0 W/cm2.

60. A computer program product for evaluating a blood vessel and/or cardiac tissue in a subject comprising:

a computer readable medium having computer readable program code embodied therein, the computer readable program code comprising computer readable program code configured to detect a mechanical property of a vessel wall and/or cardiac tissue to provide at least first and second values associated with the mechanical property at at least two timing points during a cardiac cycle of the subject; and computer readable program code configured to compare the first and second values, and, computer readable program code configured to evaluate the blood vessel and or cardiac tissue as a result of the value comparison.

61. A computer readable program product for evaluating a blood vessel and/or cardiac tissue in a subject comprising:

a computer readable medium having computer readable program embodied therein, the computer readable program code comprising computer readable program code configured to detect a first value associated with a mechanical property of a vessel wall and/or cardiac tissue at a first spatial point within a first layer of the vessel wall and/or cardiac tissue;

computer readable program code configured to detect a second value associated with the mechanical property at a second spatial point of the vessel wall and/or cardiac tissue within a second layer of the vessel wall and/or cardiac tissue; and computer readable program code configured to compare the first and second values and, computer readable program code configured to evaluate the blood vessel and or cardiac tissue as a result of the value.

62. An ultrasound system comprising:
an ultrasound transducer array controller configured to deliver a pushing pulse for between about 0.025 to about 10 milliseconds from an ultrasound transducer array having a plurality of elements to a target region within a medium to displace the target region to a displaced position, to deliver a tracking pulse from the ultrasound transducer array to the target region, and to receive a plurality of tracking signals from locations in the target region, each tracking signal being responsive to the tracking pulse, and to form parallel beamformed signals from the plurality of tracking signals.

63. A system according to claim 62 wherein the tracking signal detects the displaced position of the target region.

64. A system according to claim 62 wherein the ultrasound transducer array controller is further configured to deliver an initial tracking pulse from the ultrasound transducer array to the target region prior to the pushing pulse, and to receive an initial tracking signal responsive to the tracking pulse in the target region to detect an initial position for the target region;

65. A system according to claim 64 wherein the tracking pulses comprises a de-focused beam with respect to the target region.

66. A system according to claim 64 wherein the tracking signals comprise multiple sums of differently focused delayed signals received at each of the plurality of elements in the ultrasound transducer array.

67. A system according to claim 64 wherein the ultrasound transducer array controller is further configured to deliver the tracking pulse by delivering the tracking pulse at a first intensity level, and to deliver a pushing pulse by delivering the pushing pulse at a second intensity level that is greater than the first intensity level.

68. A system according to claim 67 wherein the ultrasound transducer array controller is further configured to deliver an initial tracking pulse by delivering the initial tracking pulse at the first intensity level.

69. A system according to claim 67 wherein the second intensity level is a range between about 10.0 W/cm2 and about 1000.0 W/cm2.

70. A system according to claim 67 wherein the first intensity level is about 0.72 W/cm2.

71. A system for evaluating a blood vessel and/or cardiac tissue in a subject comprising:
an ultrasound transducer array controller configured to deliver an acoustic radiation force pulse to the blood vessel and/or cardiac tissue and to detect a mechanical property of a vessel wall and/or cardiac tissue responsive to the acoustic radiation force pulse to provide at least first and second values associated with the mechanical property at at least two timing points during a cardiac cycle of the subject, and to compare the first and second values, and to evaluate a blood vessel and/or cardiac tissue as a result of the comparison.

72. A system according to claim 71 wherein a target region comprises blood vessel wall and/or cardiac tissue and wherein the ultrasound transducer array controller is further configured to detect a mechanical property by
delivering a first tracking pulse from an ultrasound transducer array having a plurality of elements to a target region within a medium;
receiving a first set of tracking signals from locations in the target region responsive to the tracking pulse in the target region to detect an initial position for the target region;
delivering a pushing pulse from the ultrasound transducer array to the target region to displace the target region to a displaced position;
delivering a second tracking pulse from the ultrasound transducer array to the target region; and
receiving a second set of tracking signals from locations in the target region responsive to the second tracking pulse in the target region to detect the displaced position of the target region.

73. A system according to claim 72 wherein:
the ultrasound transducer array controller is further configured to deliver the first tracking pulse by delivering the first tracking pulse at a first intensity level, and to deliver a pushing pulse by delivering the pushing pulse at a second intensity level that is greater than the first intensity level.

74. A system according to claim 72 wherein:
the ultrasound transducer array controller is further configured to deliver a second tracking pulse by delivering the second tracking pulse at the first intensity level.

75. A system according to claim 72 wherein the second intensity level is a range between about 1.0 W/cm2 and about 10,000.0 W/cm2.

76. A system according to claim 72 wherein the first intensity level is less than about 1.0 W/cm2.

77. A system according to claim 72 wherein the step of delivering a pushing pulse comprises delivering the pushing pulse for between about 0.025 to about 0.5 milliseconds.

78. A system for evaluating a blood vessel and/or cardiac tissue in a subject comprising:
an ultrasound transducer array controller configured to deliver an acoustic radiation force pulse to the blood vessel and/or cardiac tissue and to detect a first value associated with a mechanical property of a vessel wall and/or cardiac tissue responsive to the acoustic radiation force pulse at a first spatial point within a first layer of the vessel wall and/or cardiac tissue, to detect a second value associated with the mechanical property at a second spatial point of the vessel wall and/or cardiac tissue within a second layer of the vessel wall and/or cardiac tissue, to compare the first and second values, and to evaluate a blood vessel and/or cardiac tissue as a result of the value comparison.

79. A system according to claim 78 wherein a target region comprises blood vessel wall and/or cardiac tissue and wherein the ultrasound transducer array controller is further configured to detect a mechanical property by
delivering a first tracking pulse from an ultrasound transducer array having a plurality of elements to a target region within a medium;
receiving a first set of tracking signals from locations in the target region responsive to the tracking pulse in the target region to detect an initial position for the target region;
delivering a pushing pulse from the ultrasound transducer array to the target region to displace the target region to a displaced position;
delivering a second tracking pulse from the ultrasound transducer array to the target region; and
receiving a second set of tracking signals from locations in the target region responsive to the second tracking pulse in the target region to detect the displaced position of the target region.

80. A system according to claim 79 wherein:
the ultrasound transducer array controller is configured to deliver the first tracking pulse by delivering the first tracking pulse at a first intensity level, and to deliver a pushing pulse by delivering the pushing pulse at a second intensity level that is greater than the first intensity level.

81. A system according to claim 80 wherein:

the ultrasound transducer array controller is further configured to deliver a second tracking pulse by delivering the second tracking pulse at the first intensity level.

82. A system according to claim 80 wherein the second intensity level is a range between about 1.0 W/cm2 and about 10,000.0 W/cm2.

83. A system according to claim 80 wherein the first intensity level is less than about 1.0 W/cm2.

84. A system according to claim 80 wherein the ultrasound transducer array controller is further configured to deliver a pushing pulse by delivering the pushing pulse for between about 0.025 and about 0.5 milliseconds.

* * * * *

UNITED STATES PATENT AND TRADEMARK OFFICE
CERTIFICATE OF CORRECTION

PATENT NO. : 7,374,538 B2  Page 1 of 1
APPLICATION NO. : 10/680073
DATED : May 20, 2008
INVENTOR(S) : Nightingale et al.

It is certified that error appears in the above-identified patent and that said Letters Patent is hereby corrected as shown below:

Column 18, Claim 6, Line 10: Please correct "about 1.0 W/cm2and about"
To read -- about 1.0 W/cm2 and about --

Column 23, Claim 61, Line 4: Please correct "value."
To read -- value comparison. --

Signed and Sealed this

Twenty-ninth Day of July, 2008

JON W. DUDAS
*Director of the United States Patent and Trademark Office*